(12) United States Patent
Hansen et al.

(10) Patent No.: US 11,918,506 B2
(45) Date of Patent: *Mar. 5, 2024

(54) MEDICAL APPLIANCE WITH SELECTIVE SENSOR POINTS AND RELATED METHODS

(71) Applicant: Coloplast A/S, Humlebaek (DK)

(72) Inventors: Jais Ask Hansen, Jaegerspris (DK); Lars Erup Larsen, Maaloev (DK); Niels Hvid, Vedbaek (DK); Finn Speiermann, Virum (DK); Klaus Thoegersen, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 490 days.

This patent is subject to a terminal disclaimer.

(21) Appl. No.: 16/955,793

(22) PCT Filed: Dec. 20, 2018

(86) PCT No.: PCT/DK2018/050391
§ 371 (c)(1),
(2) Date: Jun. 19, 2020

(87) PCT Pub. No.: WO2019/120435
PCT Pub. Date: Jun. 27, 2019

(65) Prior Publication Data
US 2020/0337883 A1   Oct. 29, 2020

(30) Foreign Application Priority Data

Dec. 22, 2017   (DK) .......................... PA 2017 70992

(51) Int. Cl.
*A61F 5/44*   (2006.01)
*A61F 5/443*   (2006.01)

(52) U.S. Cl.
CPC ............ *A61F 5/4404* (2013.01); *A61F 5/443* (2013.01)

(58) Field of Classification Search
CPC ........ A61F 5/4404; A61F 5/443; A61F 5/445; A61F 5/44; A61F 13/0246; A61F 13/42;
(Continued)

(56) References Cited

U.S. PATENT DOCUMENTS 2,054,535 A   9/1936   Diack
2,327,514 A   8/1943   Fenwick
(Continued)

FOREIGN PATENT DOCUMENTS

CN   203786580 U   8/2014
CN   104902399 A   9/2015
(Continued)

*Primary Examiner* — Benjamin J Klein
*Assistant Examiner* — Hans Kaliher
(74) *Attorney, Agent, or Firm* — Coloplast Corp., Coloplast A/S; Nick Baumann

(57) ABSTRACT

Embodiments of a base plate and/or a sensor assembly part of an ostomy appliance including selective sensor points are disclosed. The base plate and/or the sensor assembly part comprises: a first adhesive layer and a plurality of electrodes located distally of the adhesive layer. The first adhesive layer comprises a stomal opening with a center point, a proximal surface configured to be attached to a skin surface of a user, and a plurality of sensor point openings arranged circumferentially around the center point at respective radial distances. The plurality of electrodes comprises a first leakage electrode and a second leakage electrode. A sensing part of the first leakage electrode aligns with a first sensor point opening of the plurality of sensor point openings. And, a sensing part of the second leakage electrode aligns with a second sensor point opening of the plurality of sensor point openings to form a leak sensor.

20 Claims, 11 Drawing Sheets

US 11,918,506 B2
Page 2

(58) Field of Classification Search
CPC ........ A61F 13/02; A61M 1/90; A61B 5/4851;
G01N 27/20; G01N 27/041
See application file for complete search history.

(56) References Cited

U.S. PATENT DOCUMENTS

| | | |
|---|---|---|
| 2,542,233 A | 2/1951 | Carroll |
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries, Jr. et al. |
| 5,834,009 A | 11/1998 | Sawers et al. |
| 5,879,292 A | 3/1999 | Sternberg et al. |
| 6,015,399 A | 1/2000 | Mracna et al. |
| 6,025,725 A | 2/2000 | Gershenfeld et al. |
| 6,057,689 A | 5/2000 | Saadat |
| 6,103,033 A | 8/2000 | Say et al. |
| 6,135,986 A | 10/2000 | Leisner et al. |
| 6,165,005 A | 12/2000 | Mills et al. |
| 6,171,289 B1 * | 1/2001 | Millot .................. A61F 5/443 604/336 |
| 6,206,864 B1 | 3/2001 | Kavanagh et al. |
| 6,246,330 B1 | 6/2001 | Nielsen |
| 6,297,422 B1 | 10/2001 | Hansen et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | Von Dyck et al. |
| 6,520,943 B1 | 2/2003 | Wagner |
| 6,524,675 B1 | 2/2003 | Mikami et al. |
| 6,659,989 B1 | 12/2003 | Otto |
| 6,764,474 B2 | 7/2004 | Nielsen et al. |
| 7,049,478 B1 | 5/2006 | Smith |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,221,279 B2 | 5/2007 | Nielsen |
| 7,326,190 B2 | 2/2008 | Botten |
| 7,341,578 B2 | 3/2008 | von Bulow et al. |
| 7,347,844 B2 | 3/2008 | Cline et al. |
| 7,367,965 B2 | 5/2008 | Poulsen et al. |
| 7,422,578 B2 | 9/2008 | Shan et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,449,471 B2 | 5/2013 | Tran |
| 8,474,338 B2 | 7/2013 | Gelman et al. |
| 8,500,718 B2 | 8/2013 | Locke et al. |
| 8,632,492 B2 | 1/2014 | DeLegge |
| 8,680,991 B2 | 3/2014 | Tran |
| 8,684,982 B2 | 4/2014 | Nguyen-DeMary et al. |
| 8,740,865 B2 | 6/2014 | Krystek et al. |
| 8,795,257 B2 | 8/2014 | Coulthard et al. |
| D712,545 S | 9/2014 | Igwebuike et al. |
| 8,821,464 B2 | 9/2014 | Hanuka et al. |
| 8,975,465 B2 | 3/2015 | Hong et al. |
| 8,979,813 B2 | 3/2015 | Uveborn |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,779 B2 | 4/2017 | Grum-Schwensen et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,306,224 B2 | 4/2022 | Chatterjee et al. |
| 11,406,525 B2 | 8/2022 | Seres et al. |
| 11,471,318 B2 | 10/2022 | Hansen et al. |
| 11,491,042 B2 | 11/2022 | Seres et al. |
| 11,534,323 B2 | 12/2022 | Hansen et al. |
| 11,540,937 B2 | 1/2023 | Hansen et al. |
| 11,547,595 B2 | 1/2023 | Hansen et al. |
| 11,547,596 B2 | 1/2023 | Hansen et al. |
| 11,559,423 B2 | 1/2023 | Speiermann et al. |
| 11,559,426 B2 | 1/2023 | Sletten et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise, Jr. et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |

(56) References Cited

U.S. PATENT DOCUMENTS

| | | |
|---|---|---|
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0010256 A1 | 1/2007 | Klabunde et al. |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow, Jr. et al. |
| 2008/0091154 A1 | 4/2008 | Botten |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1* | 2/2010 | Thirstrup .............. A61F 5/4404 340/657 |
| 2010/0036206 A1 | 2/2010 | Lorio |
| 2010/0072271 A1 | 3/2010 | Thorstensson |
| 2010/0076275 A1 | 3/2010 | Chu et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0231620 A1 | 9/2013 | Thirstrup et al. |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0128815 A1 | 5/2014 | Cabiri et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0351690 A1 | 12/2015 | Toth et al. |
| 2015/0374896 A1 | 12/2015 | Du et al. |
| 2016/0015570 A1 | 1/2016 | Heinecke et al. |
| 2016/0084869 A1 | 3/2016 | Yuen et al. |
| 2016/0117062 A1 | 4/2016 | Hussam et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0178387 A1 | 6/2016 | Yamasaki et al. |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mårtensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | DiMaio et al. |
| 2017/0079576 A1 | 3/2017 | Stroebech et al. |
| 2017/0098044 A1 | 4/2017 | Lai et al. |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0319073 A1 | 11/2017 | DiMaio et al. |
| 2017/0340474 A1 | 11/2017 | Thirstrup et al. |
| 2017/0348137 A1 | 12/2017 | Hvid et al. |
| 2017/0360592 A1 | 12/2017 | Carrubba |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0171183 A1 | 6/2018 | Sakurai et al. |
| 2018/0177626 A1 | 6/2018 | Israelson |
| 2018/0250156 A1 | 9/2018 | Lam |
| 2018/0298240 A1 | 10/2018 | Chatterjee et al. |
| 2018/0344533 A1 | 12/2018 | Rovaniemi |
| 2019/0008439 A1 | 1/2019 | Sageder et al. |
| 2019/0099552 A1 | 4/2019 | Zhang et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Herencia |
| 2020/0297244 A1 | 9/2020 | Brownhill et al. |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |

(56) References Cited

U.S. PATENT DOCUMENTS

| | | |
|---|---|---|
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2022/0000652 A1 | 1/2022 | Thirstrup et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0378602 A1 | 12/2022 | Hansen et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0145670 A1 | 5/2023 | Seres et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 69722993 T2 | 7/2004 |
| DE | 102011014321 A1 | 9/2012 |
| DE | 102011076219 A1 | 11/2012 |
| EP | 0168967 A1 | 1/1986 |
| EP | 0373782 B1 | 10/1994 |
| EP | 0416397 B1 | 5/1995 |
| EP | 0896211 A2 | 2/1999 |
| EP | 0800804 B1 | 6/2003 |
| EP | 1188157 B1 | 12/2005 |
| EP | 2108345 A1 | 10/2009 |
| EP | 1275357 B1 | 3/2011 |
| EP | 2000083 B1 | 8/2012 |
| EP | 2601915 A1 | 6/2013 |
| EP | 2738960 A1 | 6/2014 |
| EP | 2489561 B1 | 8/2014 |
| EP | 2453851 B1 | 10/2014 |
| EP | 2654646 B1 | 7/2016 |
| EP | 3226946 A1 | 10/2017 |
| EP | 3213727 B1 | 12/2019 |
| EP | 3064179 B1 | 9/2021 |
| GB | 2219679 A | 12/1989 |
| GB | 2308306 B | 9/1999 |
| GB | 2343628 A1 | 5/2000 |
| GB | 2465742 B | 7/2012 |
| GB | 2486968 B | 2/2015 |
| GB | 2542093 A | 3/2017 |
| GB | 2561193 B | 9/2020 |
| JP | H0474882 A | 3/1992 |
| JP | H06152077 A | 5/1994 |
| JP | H0910184 A | 1/1997 |
| JP | H11128352 A | 5/1999 |
| JP | 2000093448 A | 4/2000 |
| JP | 2001087299 A | 4/2001 |
| JP | 2002055074 A | 2/2002 |
| JP | 2002224093 A | 8/2002 |
| JP | 2005323981 A | 11/2005 |
| JP | 2007319561 A | 12/2007 |
| JP | 2009519751 A | 5/2009 |
| JP | 2014033745 A | 2/2014 |
| JP | 2014054368 A | 3/2014 |
| JP | 2014507182 A | 3/2014 |
| KR | 101056989 B1 | 8/2011 |
| KR | 20120003987 A | 1/2012 |
| KR | 200485138 Y1 | 12/2017 |
| NL | 1001019 C2 | 2/1997 |
| NL | 1003904 C2 | 3/1998 |
| TW | 201201783 A | 1/2012 |
| WO | 1994015562 A1 | 7/1994 |
| WO | 1997010012 A1 | 3/1997 |
| WO | 9933037 A1 | 7/1999 |
| WO | 1999036017 A1 | 7/1999 |
| WO | 0079497 A1 | 12/2000 |
| WO | 2001013830 A1 | 3/2001 |
| WO | 2001050996 A1 | 7/2001 |
| WO | 2002052302 A2 | 7/2002 |
| WO | 2002099765 A1 | 12/2002 |
| WO | 2005038693 A1 | 4/2005 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007070266 A1 | 6/2007 |
| WO | 2007098762 A1 | 9/2007 |
| WO | 2007128038 A1 | 11/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009107011 A2 | 9/2009 |
| WO | 2009112912 A2 | 9/2009 |
| WO | 2011003421 A1 | 1/2011 |
| WO | 2011004165 A1 | 1/2011 |
| WO | 2011061540 A1 | 5/2011 |
| WO | 2011105701 A2 | 9/2011 |

(56) References Cited

FOREIGN PATENT DOCUMENTS

| | | |
|---|---|---|
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2012084987 A2 | 6/2012 |
| WO | 2013013197 A1 | 1/2013 |
| WO | 2013095231 A1 | 6/2013 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2015094064 A1 | 6/2015 |
| WO | 2015187366 A1 | 12/2015 |
| WO | 2016132738 A1 | 8/2016 |
| WO | 2016162038 A1 | 10/2016 |
| WO | 2016166731 A1 | 10/2016 |
| WO | 2016192738 A1 | 12/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017074505 A1 | 5/2017 |
| WO | 2017088153 A1 | 6/2017 |
| WO | 2017108109 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019120432 A1 | 6/2019 |
| WO | 2019161859 A1 | 8/2019 |
| WO | 2019161860 A1 | 8/2019 |
| WO | 2019161863 A1 | 8/2019 |
| WO | 2019174693 A1 | 9/2019 |
| WO | 2019174695 A1 | 9/2019 |
| WO | 2019213623 A1 | 11/2019 |
| WO | 2020035121 A1 | 2/2020 |

* cited by examiner

MEDICAL APPLIANCE WITH SELECTIVE SENSOR POINTS AND RELATED METHODS

RELATED METHODS

The present disclosure relates to an ostomy system, devices thereof and method for monitoring an ostomy appliance. The ostomy appliance system comprises an ostomy appliance and an ostomy monitor device. In particular, the present disclosure relates to leakage detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
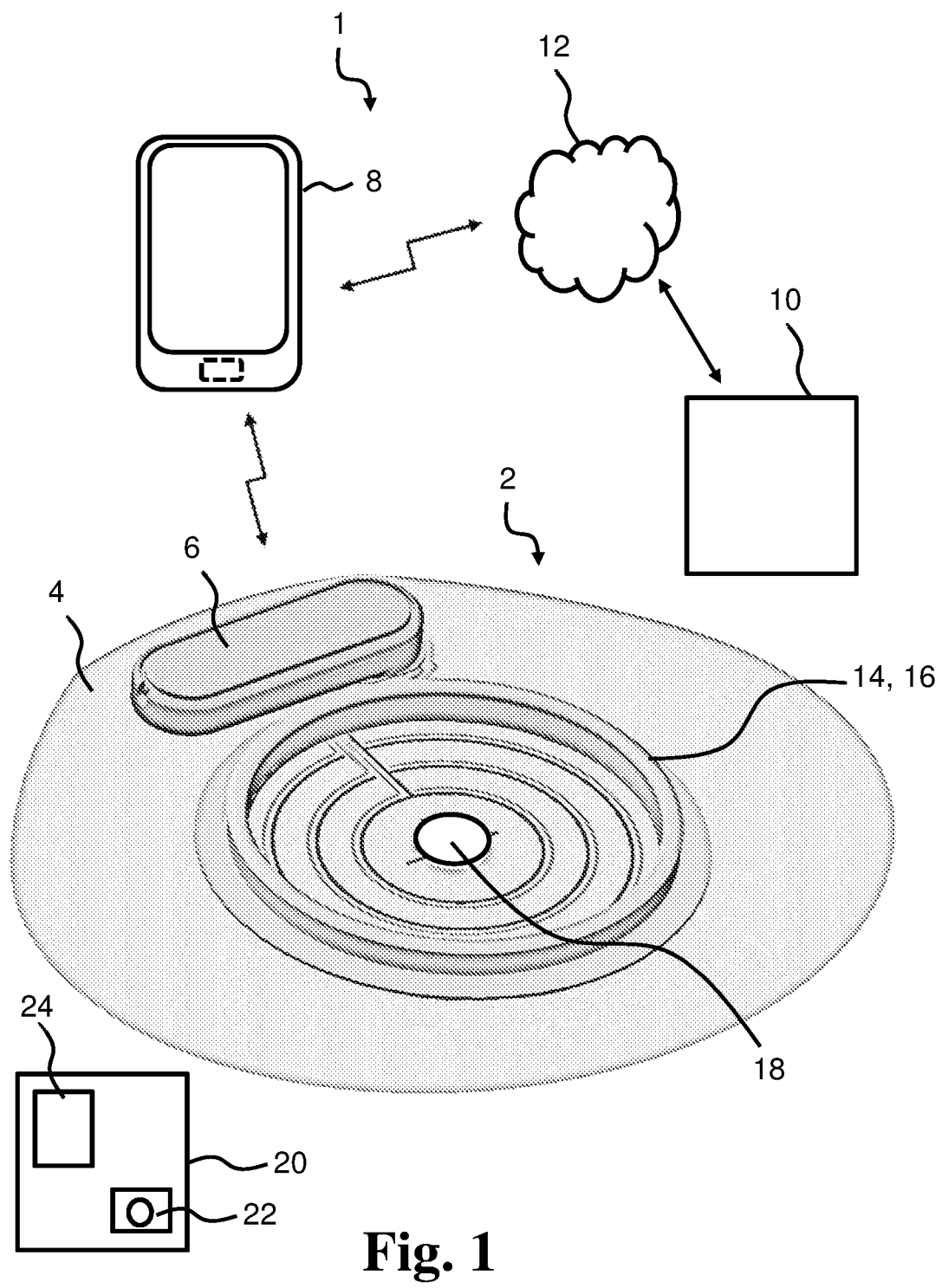
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc.

Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocoloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, such as a leakage electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. In embodiments, the electrode layer may be formed as a water sealing or a water transparent structure to allow water transport from the first adhesive layer to the second adhesive layer. An electrode comprises a connection part for connecting the respective electrode to other components and/or interface terminals/terminal elements. An electrode may comprise one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage. The sensing part may be suitable for sensing, e.g. by its shape, said shape potentially being circular, oval, or rectangular. Thus, the conductor part may conduct a signal arising from the sensing part. An electrode may comprise alternating conductor parts and sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and/or carbonaceous (e.g. carbon black, carbon nanotube, carbon fibre, graphene, graphite) materials.

Two electrodes of the electrode assembly may form a sensor, e.g. a leak sensor and/or an erosion sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The one or more electrodes may comprise one or more leakage electrodes, such as a first leakage electrode, a second leakage electrode, and/or a third leakage electrode. Additionally or alternatively, the one or more electrodes may comprise one or more erosion electrodes, such as a first erosion electrode, a second erosion electrode, and/or a third erosion electrode. The one or more leakage electrodes, such as the fourth electrode and/or the fifth electrode and/or the sixth electrode, may be configured to detect leakage or an imminent leakage, e.g. the one or more leakage electrodes may partly be exposed via sensor point openings. The one or more erosion electrodes, such as the first electrode and/or the second electrode and/or the third electrode, may be configured to detect erosion of an adhesive layer, such as the first adhesive layer, e.g. by detecting water content in the adhesive layer, e.g. by detecting increased conductivity through the adhesive layer.

For example, the first electrode and the ground electrode (e.g. first electrode part of the ground electrode) may form a first erosion sensor. The second electrode and the ground electrode (e.g. second electrode part of the ground electrode) may form a second erosion sensor. The third electrode and the ground electrode (e.g. third electrode part of the ground electrode) may form a third erosion sensor. The fourth electrode and the ground electrode (e.g. fourth electrode part of the ground electrode) may form a first leakage sensor. The fifth electrode and the ground electrode (e.g. fifth electrode part of the ground electrode) may form a second leakage sensor.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU).

The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part may comprise a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or of the sensor assembly part, such as of the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part. Additionally or alternatively, the first intermediate element may be less absorbing, such as water and/or sweat absorbing, than the first adhesive layer.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates and/or sensor assembly parts, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determining an operating state of the base plate and/or the sensor assembly part of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate and/or the sensor assembly part via the second interface; and/or in accordance with a determination that the operating state is a second operating state, transmit a second monitor signal comprising monitor data indicative of the second operating state of the base plate and/or the sensor assembly part via the second interface.

In one or more exemplary monitor devices, the first operating state of the base plate and/or the sensor assembly part corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate and/or the sensor assembly part corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate and/or the sensor assembly part is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate and/or the sensor assembly part may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by $$(P\_1\_1 < TH\_1\_1),$$

$$(P\_2\_1 > TH\_1\_2), \text{ and}$$

$$(P\_3\_1 > TH\_1\_3),$$

wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value, and wherein the first operating state is indicative of low degree of radial erosion on the base plate and/or the sensor assembly part. The first threshold values (TH_1_1, TH_1_2 and TH_1_3) may be the same or different, e.g. depending on the electrode configuration of the base plate and/or the sensor assembly part. The first tertiary criterion (P_3_1<TH_1_3) may be omitted in the first criteria set.

The first primary parameter P_1_1 may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate and/or the sensor assembly part is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate and/or the sensor assembly part is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by ($P\_1\_1 < TH\_2\_1$), ($P\_2\_1 < TH\_2\_2$), and ($P\_3\_1 > TH\_2\_3$)

wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate and/or the sensor assembly part. The second threshold values ($TH\_2\_1$, $TH\_2\_2$ and $TH\_2\_3$) may be the same or different, e.g. depending on the electrode configuration of the base plate and/or the sensor assembly part. The second primary criterion ($P\_1\_1 < TH\_2\_1$) and/or the second tertiary criterion ($P\_3\_1 > TH\_2\_3$) may be omitted in the second criteria set.

In one or more exemplary monitor devices, to determine an operating state of the base plate and/or the sensor assembly part is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by ($P\_1\_1 > TH\_D\_1$), ($P\_2\_1 > TH\_D\_2$), and ($P\_3\_1 > TH\_D\_3$)

wherein $P\_1\_1$ is a first primary parameter based on the first parameter data and indicative of the resistance between the first electrode pair, $TH\_D\_1$ is a default primary threshold value, $P\_2\_1$ is a second primary parameter based on the second parameter data and indicative of the resistance between the second electrode pair, $TH\_D\_2$ is a default secondary threshold value, $P\_3\_1$ is a third primary parameter based on the third parameter data and indicative of the resistance between the third electrode pair, $TH\_D\_3$ is a default tertiary threshold value, and wherein the default operating state is indicative of very low or no degree of radial erosion on the base plate and/or the sensor assembly part. The default threshold values ($TH\_D\_1$, $TH\_D\_2$ and $TH\_D\_3$) may be the same or different, e.g. depending on the electrode configuration of the base plate and/or the sensor assembly part.

In one or more exemplary monitor devices, to determine an operating state of the base plate and/or the sensor assembly part is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate and/or the sensor assembly part corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by ($P\_1\_1 < TH\_3\_1$), ($P\_2\_1 < TH\_3\_2$), and ($P\_3\_1 < TH\_3\_3$)

wherein $P\_1\_1$ is a first primary parameter based on the first parameter data and indicative of the resistance between the first electrode pair, $TH\_3\_1$ is a third primary threshold value, $P\_2\_1$ is a second primary parameter based on the second parameter data and indicative of the resistance between the second electrode pair, $TH\_3\_2$ is a third secondary threshold value, $P\_3\_1$ is a third primary parameter based on the third parameter data and indicative of the resistance between the third electrode pair, $TH\_3\_3$ is a third tertiary threshold value, and wherein the third operating state is indicative of high degree of radial erosion on the base plate and/or the sensor assembly part. The third threshold values ($TH\_3\_1$, $TH\_3\_2$ and $TH\_3\_3$) may be the same or different, e.g. depending on the electrode configuration of the base plate and/or the sensor assembly part. The third primary criterion ($P\_1\_1 < TH\_3\_1$) and/or the third secondary criterion ($P\_2\_1 < TH\_3\_2$) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data, and determine an operating state of the base plate and/or the sensor assembly part of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate and/or the sensor assembly part corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by ($P\_4\_1 < TH\_4\_4$)

wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped. Additionally or alternatively, the monitor device housing may be rigid or flexible. Additionally or alternatively, the monitor device may be rigid or flexible.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery. Additionally or alternatively, the sensor terminal may change its function if the charging voltage is sensed at relevant terminals.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

The monitor device may be electrically coupled to the plurality of electrodes of the base plate and/or the sensor assembly part. For example, the monitor device may be couplable, such as releasably couplable, to the plurality of electrodes of the base plate and/or the sensor assembly part. The monitor device may be configured to measure one or more resistances between the plurality of electrodes, and detect the leakage of output based on the measured one or more resistances. Alternatively or additionally, the monitor device may be configured to measure one or more capacitances between the plurality of electrodes. The monitor device may be configured to detect leakage of output based on the measured one or more capacitances, e.g. in combination with the measured one or more resistances.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a base plate and/or a sensor assembly part for an ostomy appliance, the base plate and/or the sensor assembly part including selective sensor points for detecting leakage from the ostomy appliance, such as a base plate and/or a sensor assembly part disclosed above. The base plate and/or the sensor assembly part comprises: a first adhesive layer and a plurality of electrodes located distally of the first adhesive layer. For embodiments of the base plate and/or the sensor assembly part with selective sensor points, the first adhesive layer of the base plate and/or the sensor assembly part comprises: a stomal opening with a center point, a proximal surface configured to be attached to a skin surface of a user, and a plurality of sensor point openings arranged circumferentially around the center point at respective radial distances. For embodiments of the base plate and/or the sensor assembly part with selective sensor points, the plurality of electrodes of the base plate and/or the sensor assembly part comprises a first leakage electrode and a second leakage electrode, a sensing part of the first leakage electrode aligning with a first sensor point opening of the plurality of sensor point openings of the first adhesive layer and a sensing part of the second leakage electrode aligning with a second sensor point opening of the plurality of sensor point openings of the first adhesive layer to form a leak sensor.

That is, a base plate and/or a sensor assembly part may include a configuration for detecting leakage associated with use of an ostomy appliance. More particularly, a base plate and/or a sensor assembly part may include a first adhesive layer and a plurality of electrodes, such as at least two electrodes, that are located distally of the first adhesive layer, wherein the configuration of the first adhesive layer relative to the electrodes provides leak detection monitoring locations. A first opening of at least two openings in the first adhesive layer overlaps a portion of a first electrode of the plurality of electrodes and a second opening of the at least two openings in the first adhesive layer overlaps a portion of a second electrode of the plurality of electrodes. Although additional openings can be provided, by providing at least two openings in the first adhesive layer a leak may be detected when a leaking material spans or bridges the two openings to essentially complete the circuit between the two electrodes.

Embodiments of the base plate and/or the sensor assembly part with selective sensor points may further comprise a masking element, the masking element being arranged between a second adhesive layer and the first adhesive layer, the masking element being more insulative than the first adhesive layer.

For embodiments of the base plate and/or the sensor assembly part with selective sensor points, the masking element may comprise a plurality of sensor point openings, each sensor point opening of the first adhesive layer aligning with a sensor point opening of the masking element to form a sensor point. Additionally or alternatively, by including a masking element arranged between the conductor parts and the first adhesive layer, the conductor parts of the electrodes may be insulated from the first adhesive layer, which may prevent more than one of the conductor parts of the electrodes from short circuiting due to moisture absorption in the first adhesive layer.

In at least one embodiment, the diameters of the sensor point openings the first adhesive layer are larger than diameters of the sensor point openings of the masking element. In at least one embodiment, the masking element has more than ten sensor point openings, such as in the range from twenty to fifty sensor point openings, e.g. twenty-seven sensor point openings. In addition, in at least one embodiment the first adhesive layer has more than ten sensor point openings, such as in the range from twenty to fifty sensor point openings, e.g. twenty-seven sensor point openings, and the base plate and/or the sensor assembly part has more than ten sensor points, such as in the range from twenty to fifty sensor points, e.g. twenty-seven sensor points. In at least one embodiment, each sensor point has a diameter greater than one millimeter (e.g., 1.0 mm-4.0 mm).

A distance between two neighbouring sensor point openings in the first adhesive layer may be in the range from 1 mm to 20 mm.

A sensor point opening of the first adhesive layer may have a suitable shape and size facilitating access to a sensing part of an electrode from the proximal side of the first adhesive layer. A sensor point opening the first adhesive layer may have a circular or oval shape. A sensor point opening the first adhesive layer may have a shape of a rectangle or square optionally with rounded corners.

A minimum extension of a sensor point opening of the first adhesive layer may be at least 0.5 mm, such as at least 1 mm. A sufficiently large minimum extension reduces the risk of the first adhesive layer, due to the materials flow capabilities, closing the sensor point opening or at least partly or fully covering the sensing part of the corresponding leakage electrode.

A maximum extension of a sensor point opening of the first adhesive layer may be less than 20 mm.

An exemplary sensor point opening of the first adhesive layer may have a minimum extension, e.g. measured radially from the center point, in the range from 1 mm to 4 mm and/or a maximum extension, e.g. measured circumferentially around the center point, in the range from 2 mm to 6 mm.

In embodiments, the distance between neighbouring sensor point openings of the masking layer may be uniform or non-uniform. Additionally or alternatively, a range of distances may separate neighbouring sensor point openings of the masking layer. For example, the distances between neighbouring sensor point openings of the masking layer may be approximately 2 mm-2.5 mm. Additionally or alternatively, the distance between a sensor point opening of the masking layer and the center point of the stomal opening may be the same for each sensor point opening of the masking layer or be different for different sensor point openings of the masking layer. Additionally or alternatively, a range of distances may separate the sensor point openings of the masking layer from the center point of the stomal opening. For example, the distances between the sensor point openings of the masking layer and the center point of the stomal opening may be in the range from 20 mm to 50 mm, e.g. in the range from 25 mm to 35 mm, such as about 30 mm.

A distance between two neighbouring sensor point openings of the masking element may be in the range from 1 mm to 20 mm.

A sensor point opening of the masking element may have a suitable shape and size facilitating access to a sensing part of an electrode from the proximal side of the first adhesive layer. A sensor point opening the masking element may have a circular or oval shape. A sensor point opening the masking element may have a shape of a rectangle or square optionally with rounded corners.

A minimum extension of a sensor point opening of the masking element may be at least 0.2 mm, such as at least 0.5 mm. A maximum extension of a sensor point opening of the masking element may be less than 20 mm.

In accordance with at least one embodiment, the plurality of electrodes is configured to form a plurality of sensing sectors, such as a bottom sensing sector and lateral sensing sectors located on either side of the bottom sensing sector. However, as those skilled in the art will appreciate, a single sensing sector could be provided, or alternatively, two sensing sectors could be provided, or alternatively yet, greater than three sensing sectors could be provided, such as 4, 5, 6 or more sensing sectors, with an appropriate number of electrodes situated to accommodate the desired number of sensing sectors.

The sensor point openings and electrode positions are configured to provide a warning to the user (such as described herein, and which may include, but is not limited to one or more of a tactile warning, alert via a mobile phone and/or a wearable device such as a wrist band or watch) that a leak may occur, or be about to occur, thereby allowing the user to take action to prevent a leak or otherwise mitigate the undesirable results of a leak adjacent the user's stoma and associated with the ostomy appliance. Accordingly, a leak, as measured by a change in resistance between the electrodes included in the bottom sensing sector and/or one of the two lateral sensing sectors, may be sensed by, for example, the monitor device. When the resistance between two of the fourth electrode, the fifth electrode, and the fourth electrode part of the ground electrode decreases below a threshold level, the monitor device may send an indication to the user that a leak is predicted, thereby allowing the user to take action. For example, the monitor device may send a signal to the user suggesting the user change his/her ostomy appliance and/or base plate.

Embodiments of the base plate with selective sensor points may further comprise a filling material disposed in each sensor point. More particularly, in at least one embodiment, a filling material is disposed in the sensor point and/or is otherwise situated adjacent at least a portion of the sensing part of the fourth electrode, fifth electrode and fourth electrode part (connected to the ground electrode) associated with sensor point openings of the first adhesive layer, and sensor point openings of the masking element. In embodiments, the filling material may include a proximal surface that is substantially level with adjacent portions of the proximal surface of the first adhesive layer. Alternatively, the filling material may have a proximal surface that is not level with adjacent portions of the proximal surface of the first adhesive layer. In embodiments, the filling material is preferably a structurally supportive material to maintain the sensing point pathway to the sensing part, such as when the base plate and/or the sensor assembly part is packaged and/or is being transported. The filling material may be provided on a release liner of the base plate and/or sensor assembly part, as describe in further detail above. For example, the release liner may form the filling material, e.g. the release liner may comprise the filling material. The release liner may comprise protrusions for being disposed in each sensor point.

For embodiments including a filling material, the filling material may improve the structural integrity of the selective sensor points by maintaining a leakage pathway to sensing parts of the electrodes.

For embodiments of the base plate and/or the sensor assembly part with selective sensor points, diameters of the sensor point openings of the first adhesive layer may be larger than diameters of the sensor point openings of the masking element. For embodiments with a masking element having a sensor point opening smaller in size than the sensor point opening in the first adhesive layer, the difference in opening size may improve the structural integrity of the selective sensor points by maintaining a leakage pathway to sensing parts of the electrodes because the thickness transition between the proximal surface of the first adhesive layer to the surface of the electrode sensing part is gradual.

In embodiments, the distance between neighbouring sensor point openings of the first adhesive layer may be uniform or non-uniform. Additionally or alternatively, a range of distances may separate neighbouring sensor point openings of the first adhesive layer 4. For example, the distances between neighbouring sensor point openings of the first adhesive layer may be approximately 2 mm-2.5 mm. Additionally or alternatively, the distance between a sensor point opening of the first adhesive layer and the center point of the stomal opening may be the same for each sensor point opening of the first adhesive layer or be different for different sensor point openings of the first adhesive layer. Additionally or alternatively, a range of distances may separate the sensor point openings of the first adhesive layer from the center point of the stomal opening. For example, the distances between the sensor point openings of the first adhesive layer and the center point of the stomal opening may be in the range from 20 mm to 50 mm, e.g. in the range from 25 mm to 35 mm, such as about 30 mm.

For embodiments of the base plate and/or the sensor assembly part with selective sensor points, each sensor point opening may be approximately oval in shape, that is, generally oblong, in an axial direction, and may vary in size, such as having a maximum dimension of between 1 mm and 3 mm.

For embodiments of the base plate and/or the sensor assembly part with selective sensor points, the plurality of electrodes may form a plurality of sensing sectors, wherein two electrodes of the plurality of electrodes form each sensing sector. By including different sensing sectors, the location of a leak can be identified.

For embodiments of the base plate and/or the sensor assembly part with selective sensor points, each electrode of the plurality of electrodes may form two sensing sectors of the plurality of sensing sectors.

For embodiments of the base plate and/or the sensor assembly part with selective sensor points, the plurality of sensor point openings may extend through the first adhesive layer.

For embodiments of the base plate and/or the sensor assembly part with selective sensor points, the second plurality of sensor point openings may extend through the masking element.

For embodiments of the base plate and/or the sensor assembly part with selective sensor points, the respective radial distances may be generally equal distances from the center point. By utilizing generally equal radial distances from the center point to the selective sensor points, the travel time for output to selective sensor points is closer in time to each sensor point than if the sensor points are located at different radial distances. That is, if a first selective sensor point is at a radius $R_1$ and a second selective sensor point is at $R_2$, where $R_2>R_1$, then the output will take longer to travel to the second selective sensor point.

For embodiments of the base plate and/or the sensor assembly part with selective sensor points, the plurality of sensor point openings may comprise a generally oval shape as viewed in an axial direction. By having a generally oval shape, the sensor point openings include a longer portion of the electrode, that is, the major axis of the ellipse, along the electrode.

A method of manufacturing a base plate and/or a sensor assembly part of an ostomy appliance with selective sensor points is also disclosed. The method comprises: forming a first adhesive layer comprising: a stomal opening with a center point, a proximal surface configured to be attached to a skin surface of a user, and a plurality of sensor point openings arranged circumferentially around the center point at respective radial distances. The method further comprises arranging a plurality of electrodes distally of the first adhesive layer, the plurality of electrodes comprising a first leakage electrode and a second leakage electrode, a sensing part of the first leakage electrode aligning with a first sensor point opening of the plurality of sensor point openings and a sensing part of the second leakage electrode aligning with a second sensor point opening of the plurality of sensor point openings to form a leak sensor.

The method may further comprise arranging a masking element between the second adhesive layer and the first adhesive layer, the masking element being more insulative than the first adhesive layer. As noted above, by including a masking element arranged between the conductor parts and the first adhesive layer, the conductor parts of the electrodes may be insulated from the first adhesive layer, which may prevent more than one of the conductor parts of the electrodes from shorting together due to moisture absorption in the first adhesive layer.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer, the accessory device 8, and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). In alternative embodiments, the ostomy pouch may be formed together with the base plate (one-part ostomy appliance). The base plate has a stomal opening 18 with a center point. The size and/or shape of the stomal opening 18 is typically adjusted by the user or nurse before application of the ostomy appliance to accommodate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
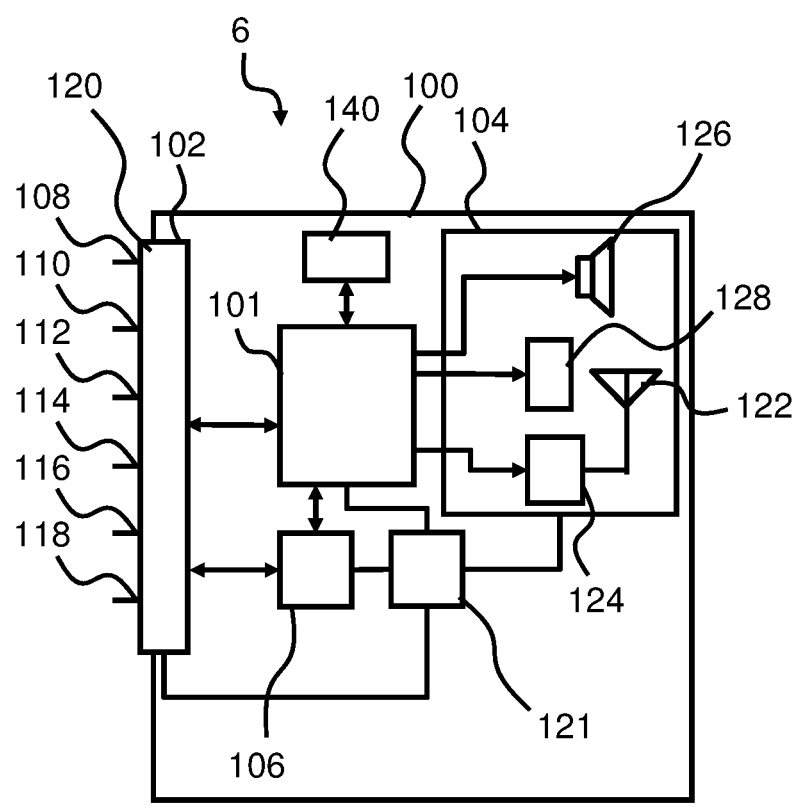
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. For example, the sensor unit 140 comprises a temperature sensor for feeding temperature data to the processor and/or a G-sensor or accelerometer for feeding acceleration data to the processor 101. Additionally or alternatively, the sensor unit 140 comprises a humidity sensor and/or an acoustic sensor. The sensor unit 140 may comprise alternative and/or additional sensors suitable and/or relevant to an ostomy system as described.

The processor 101 is configured to apply a processing scheme, and the first interface 102 is configured for collecting ostomy data from the base plate and/or the sensor assembly part coupled to the first interface, the ostomy data comprising first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate and/or the sensor assembly part of the ostomy appliance based on one or more, e.g. all, of the first parameter data, the second parameter data and the third parameter data, wherein the operating state is indicative of a degree of radial erosion of the base plate and/or the sensor assembly part and/or acute leakage risk for the ostomy appliance. The monitor device 6 is configured to, in accordance with a determination that the operating state is a first operating state, transmit a first monitor signal comprising monitor data indicative of the first operating state of the base plate and/or the sensor assembly part via the second interface; and in accordance with a determination that the operating state is a second operating state, transmit a second monitor signal comprising monitor data indicative of the second operating state of the base plate and/or the sensor assembly part via the second interface.

Figure 3:
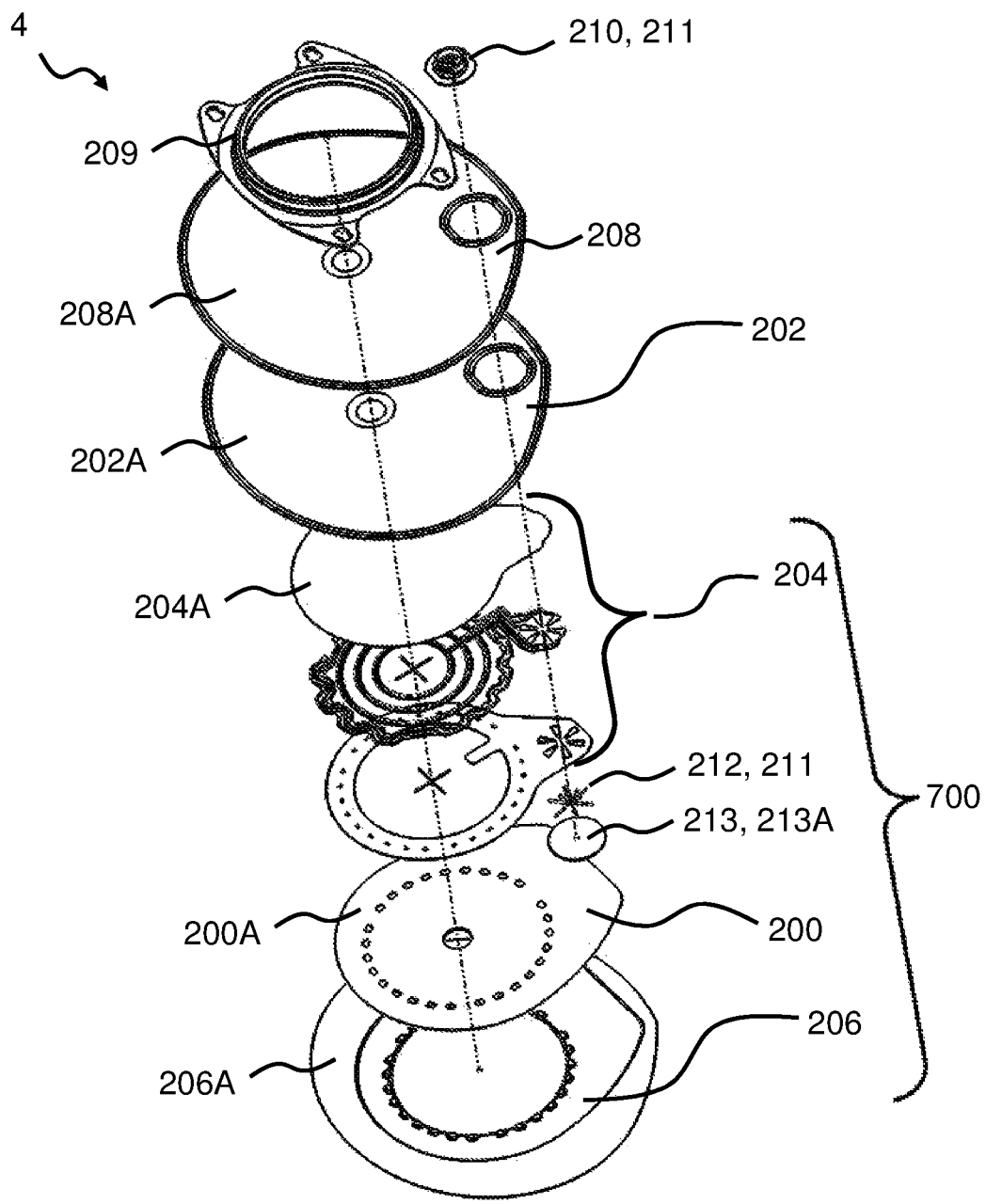
FIG. 3 is an exploded view of a base plate of an ostomy appliance.

FIG. 3 illustrates an exploded view of an exemplary base plate of an ostomy appliance. The base plate 4 comprises a first adhesive layer 200. FIG. 3 illustrates an exploded view of an exemplary base plate of an ostomy appliance. The base plate 4 comprises a first adhesive layer 200. In embodiments, the first adhesive layer 200 comprises a stomal opening 18A, which may be form part of the stomal opening 18. As stated above, the stomal opening 18 may be adjusted before application to accommodate the user's stoma, which includes adjusting the stomal opening 18A. During use, the stoma-receiving opening 18, including the stomal opening 18A, is arranged around a user's stoma and a proximal surface 200B of the first adhesive layer 200 adheres to the skin surface of the user in the peristomal area and/or to additional seals, such as sealing paste, sealing tape and/or sealing ring.

The base plate 4 optionally comprises a second adhesive layer 202, also denoted rim adhesive layer. In embodiments, the base plate 4 comprises a second adhesive layer 202, also denoted rim adhesive layer. As illustrated, the second adhesive layer 202 may be arranged distally of the first adhesive layer 200. Additionally or alternatively, a portion of the distal surface 200A of the first adhesive layer 200, which is not covered by the electrode assembly 204, may adhere to a portion of the proximal surface 202B of the second adhesive layer 202. In embodiments, the second adhesive layer 202 may have a second radial extension that is larger than a first radial extension of the first adhesive layer 200 at least in a first angular range of the base plate 4.

The first adhesive layer 200 and/or second adhesive layer 202 may comprise one or more of polyisobutenes, styrene-isoprene-styrene, and/or hydrocoloids. Different ratio of contents may change properties of the first and/or second adhesive layers 200, 202. As such, the second adhesive layer 202 and the first adhesive layer 200 may have different properties due to different ratios of polyisobutenes, styrene-isoprene-styrene, and/or hydrocoloids. For example, the second adhesive layer 202 may provide a stronger attachment to the skin compared to attachment to the skin provided by the first adhesive layer 200. Additionally or alternatively, the first adhesive layer may provide less irritation to the skin surface of a user. In embodiments, the second adhesive layer 202 may be thinner than the first adhesive layer 200. Additionally or alternatively, the second adhesive layer 202 may be less water and/or sweat absorbing than the first adhesive layer 200. Additionally or alternatively, the second adhesive layer 202 may be less mouldable than the first adhesive layer 200. The second adhesive layer 202 may provide a second barrier against leakage.

The base plate 4 comprises a plurality of electrodes arranged in an electrode assembly 204. The electrode assembly 204 is arranged between the first adhesive layer 200 and the second adhesive layer 202. For example, the electrode assembly 204 may be arranged on a distal side (e.g., the distal surface 200A) of the first resistive layer 200 and a proximal side (e.g., the proximal surface 202B) of the second resistive layer 202, The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
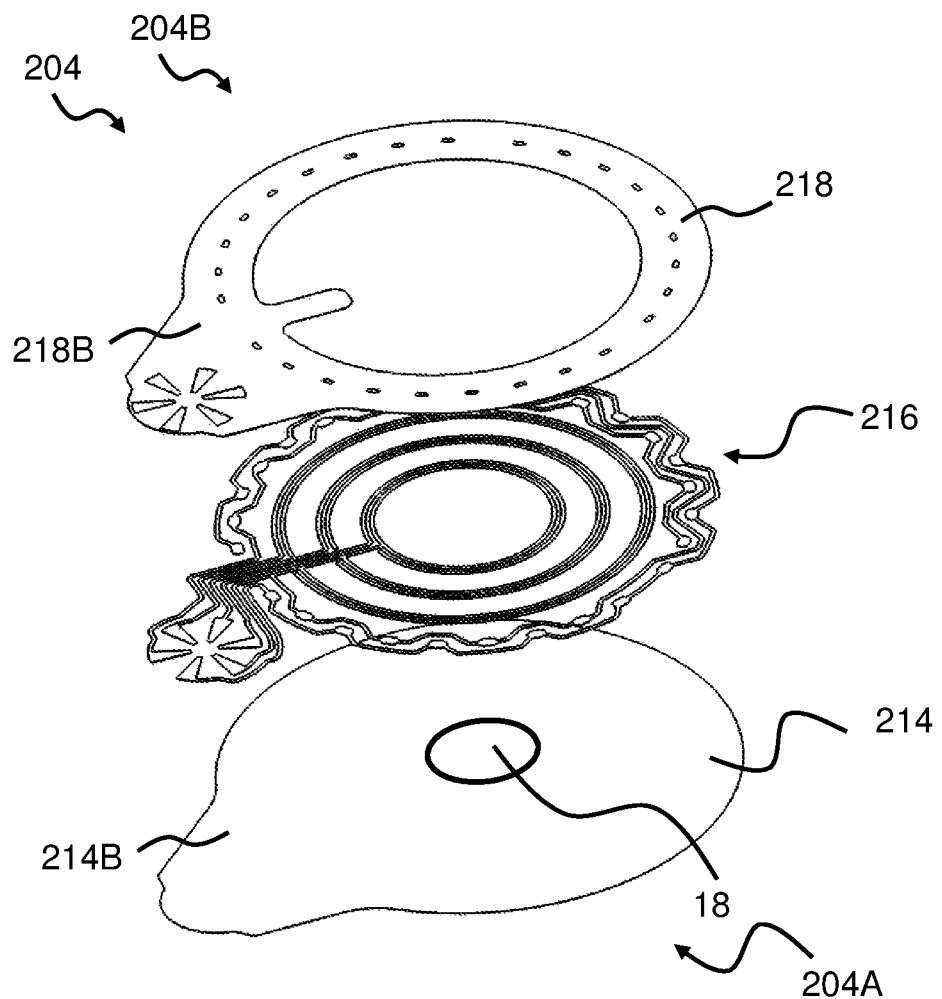
FIG. 4 is an exploded view of an exemplary electrode assembly.

FIG. 4 illustrates an exploded view of an exemplary electrode assembly 204 of a base plate and/or the sensor assembly part. The electrode assembly 204 comprises a support layer 214 with proximal surface 214B and electrodes 216 arranged on the proximal side of the support layer 214. The electrode assembly includes a ground electrode, a first electrode, a second electrode, a third electrode, a fourth electrode, and a fifth electrode, wherein each electrode has a respective connection part for connecting the electrodes to respective terminal elements of the monitor interface. In embodiments, the electrodes 216 are electrically conductive and comprise at least one of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials. Additionally or alternatively, the electrodes 216 may be made by screen-printing, inkjet-printing, direct-ink-writing, pen-plotting, 3D-printing, fused-deposition-modelling, contact-transfer printing, spray painting, chemical vapour depositing, physical vapour depositing, atomic-layer-depositing, wire-bending, and any other methods known to a person skilled in the art. In embodiments, the electrodes 216 can require one of heat-curing, UV-curing, and oxygen-activation.

In embodiments, the support layer 214 may increase the structural integrity of the electrodes 216. Additionally or alternatively, the support layer 214 may be moisture resistance or moisture transmissive. In embodiments, the support layer 214 may comprise at least one of polymeric (e.g. polyurethane, PTFE, PVDF) and ceramic (e.g. alumina, silica) materials.

Further, electrode assembly 204 comprises a masking element 218 with proximal surface 218B. In embodiments, the masking element 218 may be arranged on the distal surface 200A of the first adhesive layer 200. Additionally or alternatively, the masking element 218 may be comprised of a material that is more insulative (e.g., less electrically conductive and/or less moisture-permeable) than the first adhesive layer 200. In embodiments, the masking element 218 may comprise at least one of polymeric (e.g. polyurethane, PTFE, PVDF) and ceramic (e.g. alumina, silica) materials. The masking element 218 may cover or overlap with parts of the electrodes 216 when seen in the axial direction. As such, the masking element 218 may at least partially insulate electrode parts of the electrodes 216 from the first adhesive layer of the base plate.

Figure 5:
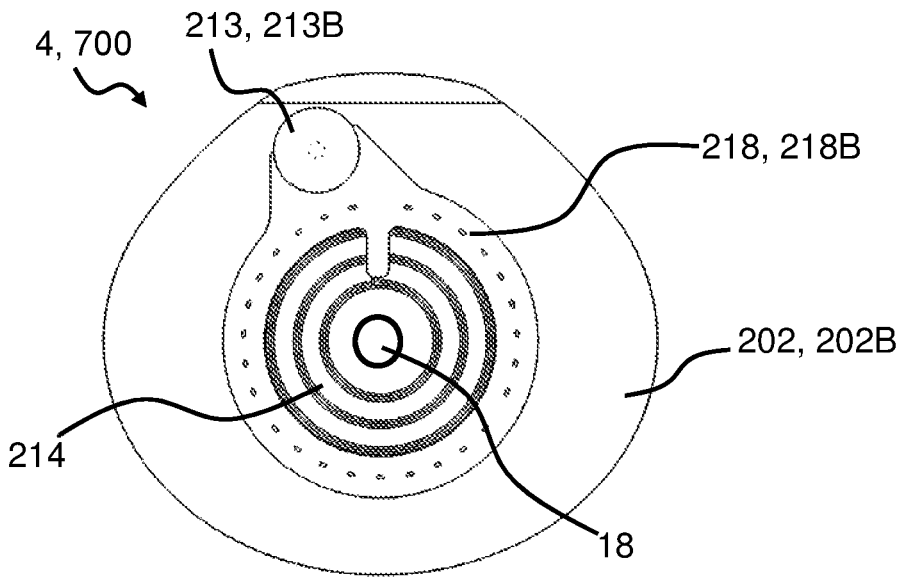
FIG. 5 is a proximal view of parts of a base plate and/or sensor assembly part.

FIG. 5 is a proximal view of proximal surfaces of base plate parts of the base plate 4 and/or the sensor assembly part 700 without the first adhesive layer 200 (illustrated in FIG. 4) and the release liner 206 (illustrated in FIG. 3). The base plate 4 and/or the sensor assembly part 700 comprises a first intermediate element 213 on the proximal side of the electrode assembly, i.e. between the electrode assembly 204 and the first adhesive layer 200. The first intermediate element 213 covers the terminal elements of the base plate 4 when seen in the axial direction and protects the first adhesive layer 200 from mechanical stress from the terminal elements of the base plate 4 and/or the sensor assembly part 700.

Figure 6:
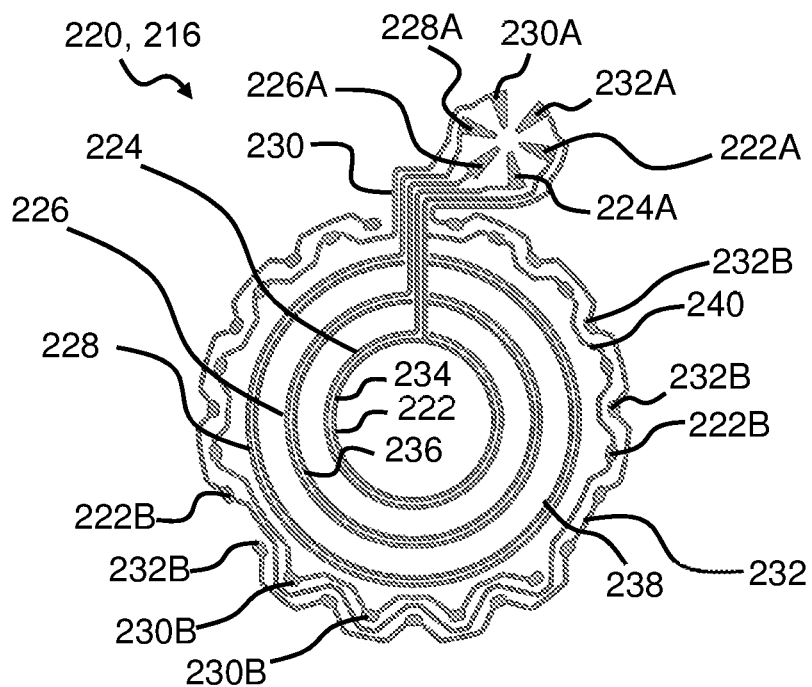
FIG. 6 is a distal view of an exemplary electrode configuration.

In embodiments, the first intermediate element 213 may facilitate protecting the terminal elements 212 and/or the connection parts 222A, 224A, 226A, 228A, 230A, 232A (see FIG. 6). For example, the first intermediate element 213 may be less compliant than the first adhesive layer 200 (depicted in FIG. 3), the second adhesive layer 202, and/or the masking element 218. By being less compliant, the first intermediate element 213 may reduce the ability of the terminal elements 212 and/or the connection parts 222A, 224A, 226A, 228A, 230A, 232A to flex. As such, the terminal elements 212 and/or the connection parts 222A, 224A, 226A, 228A, 230A, 232A may be less likely to break due to flexure. In embodiments, the first intermediate element 213 may comprise at least one of polymeric (e.g. polyurethane, PTFE, PVDF) and ceramic (e.g. alumina, silica) materials.

Additionally or alternatively, the first intermediate element 213 may reduce the likelihood that more than one of the terminal elements 212 are shorted together and/or more than one of the connection parts 222A, 224A, 226A, 228A, 230A, 232A are shorted together. For example, the first intermediate element 213 may be less moisture absorbent than the first adhesive layer 200 (depicted in FIG. 3) and/or the masking element 218. By being less moisture absorbent, the first intermediate element 213 may prevent moisture (e.g., sweat, output, etc.) from coming into contact with one or more of the terminal elements 212 and/or the connection parts 222A, 224A, 226A, 228A, 230A, 232A via the first adhesive layer 200 and/or the masking element 218 and, potentially, shorting a combination of the terminal elements 212 together and/or a combination of the connection parts 222A, 224A, 226A, 228A, 230A, 232A together.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprises a fifth connection part 232A. In embodiments, the plurality of electrodes 216 may be coupled to the monitor device 6 via the connection parts 222A, 224A, 226A, 228A, 230A, 232A. As such, the monitor device 6 may measure one or more resistances of the plurality of electrodes 216 for various purposes as described below.

The fourth electrode 230 comprises fourth sensing parts 230B. The fifth electrode 232 comprises fifth sensing parts 232B. In embodiments, parts of the fourth electrode 230 that are not the fourth connection part 230A and/or the fourth sensing parts 230B may be referred to herein as conductor parts of the fourth electrode 230. Similarly, parts of the fifth electrode 232 that are not the fifth connection part 232A and/or the fifth sensing parts 232B may be referred to herein as conductor parts of the fifth electrode 232. Additionally or alternatively, parts of the ground electrode 222 that are not part of the ground connection part 222A and/or the ground sensing parts 222B may be referred to herein as conductor parts of the ground electrode 222.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

Figure 7:
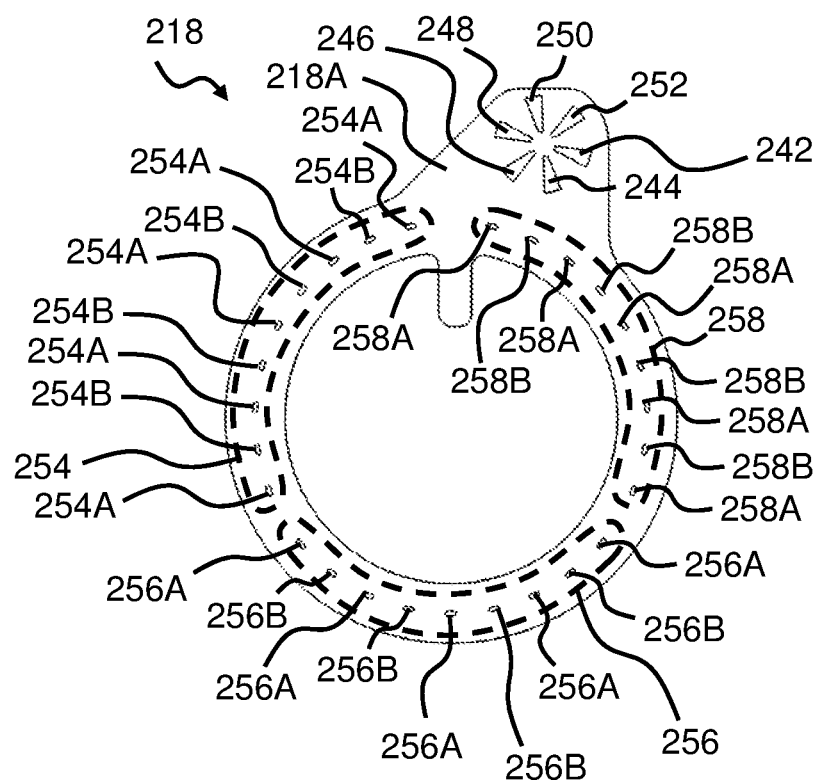
FIG. 7 is a distal view of an exemplary masking element.

FIG. 7 is a distal view of an exemplary masking element 218. In embodiments, the masking element 218 may by arranged between conductor parts of the ground electrode 222, conductor parts of the fourth electrode 230, and/or conductor parts of the fifth electrode 232. As set forth above, parts of the fourth electrode 230 that are not the fourth connection part 230A and/or the fourth sensing parts 230B may be referred to herein as conductor parts of the fourth electrode 230 (illustrated in FIG. 6). Similarly, parts of the fifth electrode 232 that are not the fifth connection part 232A and/or the fifth sensing parts 232B may be referred to herein as conductor parts of the fifth electrode 232. Additionally or alternatively, parts of the ground electrode 222 that are not part of the ground connection part 222A and/or the ground sensing parts 222B may be referred to herein as conductor parts of the ground electrode 222. Further, because the masking element 218 may be more insulative than the first adhesive layer 200, the conductor parts of the ground electrode, the fourth electrode, and the fifth electrode may be insulated from the first adhesive layer 200.

The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap (that is, axially align) with respective connection parts 222A, 224A, 226A, 228A, 230A, 232A of the electrodes of the electrode assembly. For example, connection part 222A may overlap the first terminal opening 244, connection part 224A may overlap the second terminal opening 244, connection part 226A may overlap the third terminal opening 246, connection part 228A may overlap the fourth terminal opening 250, connection part 230A may overlap the fifth terminal opening 252, and connection part 232A may overlap the sixth terminal opening 252. While the masking element 218 depicts six terminal openings, in other embodiments, the masking element 218 may include more or fewer terminal openings.

The masking element 218 has a plurality of sensor point openings. The sensor point openings comprise primary sensor point openings shown within dotted line 254. Each primary sensor point opening is configured to overlap (that is, axially align with) a ground sensing part 222B of the ground electrode 222 and/or a fourth sensing part 230B of the fourth electrode 230 of the electrode configuration 220. More particularly, the primary sensor point openings shown within dotted line 254 comprise, in the illustrated exemplary masking element, five primary first sensor point openings 254A each configured to overlap a ground sensing part 222B of the fourth electrode part 240 that is electrically connected to the ground electrode 222. In addition, the primary sensor point openings shown within dotted line 254 further comprise, in the illustrated exemplary masking element, four primary second sensor point openings 254B each configured to overlap a fourth sensing part 230B of the fourth electrode 230. In embodiments, each of the primary sensor point openings shown within dotted line 254 may be equal distances from a center point of the stomal opening 18. Alternatively, one or more of the primary sensor point openings shown within dotted line 254 may be different distances from a center point of the stomal opening 18. While the illustrated embodiment depicts five primary first sensor point openings 254A in the dotted line 254, in other embodiments, the masking element 218 includes more or fewer than five primary first sensor point openings 254A in the dotted line 254. Additionally or alternatively, while the illustrated embodiment depicts four primary second sensor point openings 254B in the dotted line 254, in other embodiments, the masking element 218 includes more or fewer than four primary second sensor point openings 254B in the dotted line 254.

Additionally or alternatively, the sensor point openings comprise secondary sensor point openings shown within dotted line 256. Each secondary sensor point opening is configured to overlap a fourth sensing part 230B of the fourth electrode 230 and/or a fifth sensing part 232B of the fifth electrode 232. More particularly, the secondary sensor point openings shown within dotted line 256 comprise, in the illustrated exemplary masking element, five secondary first sensor point openings 256A each configured to overlap a fifth sensing part 232B of the fifth electrode 232. In addition, the secondary sensor point openings shown within dotted line 256 further comprise, in the illustrated exemplary masking element, four secondary second sensor point openings 256B each configured to overlap a fourth sensing part 230B of the fourth electrode 230. In embodiments, each of the secondary sensor point openings shown within dotted line 256 may be equal distances from a center point of the stomal opening 18. Alternatively, one or more of the secondary sensor point opening shown within dotted line 256 may be different distances from a center point of the stomal opening 18. In embodiments, the secondary sensor point openings shown within dotted line 256 may be substantially the same distance from a center point of the stomal opening 18 as the primary sensor point openings shown within dotted line 254. Alternatively, one or more of the secondary sensor point openings shown within dotted line 256 may be different distance(s) from a center point of the stomal opening 18 as one or more of the primary sensor point openings shown within dotted line 254. While the illustrated embodiment depicts five secondary first sensor point openings 256A in the dotted line 256, in other embodiments, the masking element 218 includes more or fewer than five secondary first sensor point openings 256A in the dotted line 256. Additionally or alternatively, while the illustrated embodiment depicts four secondary second sensor point openings 256B in the dotted line 256, in other embodiments, the masking element 218 includes more or fewer than four secondary second sensor point openings 256B in the dotted line 256.

Additionally or alternatively, the sensor point openings comprise tertiary sensor point openings shown within dotted line 258. Each tertiary sensor opening is configured to overlap a fifth sensing part 232B of the fifth electrode 232 and/or a ground sensing part 222B of the fourth electrode part 240 that is electrically connected to the ground electrode 222 of the electrode configuration 220. More particularly, the tertiary sensor point openings shown within dotted line 258 comprise, in the illustrated exemplary masking element, five tertiary first sensor point openings 258A each configured to overlap a fifth sensing part 232B of the fifth electrode 232. In addition, the tertiary sensor point openings shown within dotted line 258 further comprise, in the illustrated exemplary masking element, four tertiary second sensor point openings 258B each configured to overlap a ground sensing part 222B of the fourth electrode part 240 that is electrically connected to the ground electrode 222. In embodiments, each of the tertiary sensor point openings shown within dotted line 258 may be equal distances from a center point of the stomal opening 18. Alternatively, one or more of the tertiary sensor point opening shown within dotted line 258 may be different distances from a center point of the stomal opening 18. In embodiments, the tertiary sensor point openings shown within dotted line 258 may be substantially the same distance from a center point of the stomal opening 18 as the primary sensor point openings shown within dotted line 254. Alternatively, one or more of the tertiary sensor point openings shown within dotted line 258 may be different distance(s) from a center point of the stomal opening 18 as one or more of the primary sensor point openings shown within dotted line 254. Additionally or alternatively, the tertiary sensor point openings shown within dotted line 258 may be substantially the same distance from a center point of the stomal opening 18 as the secondary sensor point openings shown within dotted line 256. Alternatively, one or more of the tertiary sensor point openings shown within dotted line 258 may be different distance(s) from a center point of the stomal opening 18 as one or more of the secondary sensor point openings shown within dotted line 256. While the illustrated embodiment depicts five tertiary first sensor point openings 258A in the dotted line 258, in other embodiments, the masking element 218 includes more or fewer than five tertiary first sensor point openings 258A in the dotted line 258. Additionally or alternatively, while the illustrated embodiment depicts four tertiary second sensor point openings 258B in the dotted line 258, in other embodiments, the masking element 218 includes more or fewer than four tertiary second sensor point openings 258B in the dotted line 258.

In embodiments, the distance between neighbouring sensor point openings shown within dotted lines 254, 256, 258 may be uniform or non-uniform. Additionally or alternatively, a range of distances may separate neighbouring sensor point openings shown within dotted lines 254, 256, 258. For example, the distances between neighbouring sensor point openings shown within dotted lines 254, 256, 258 may be approximately 2 mm-2.5 mm. Additionally or alternatively, the distance between a sensor point opening shown within dotted lines 254, 256, 258 and the center point of the stomal opening 18 may be the same for each sensor point opening shown within dotted lines 254, 256, 258 or be different for different sensor point openings shown within dotted lines 254, 256, 258. Additionally or alternatively, a range of distances may separate the sensor point openings shown within dotted lines 254, 256, 258 from the center point of the stomal opening 18. For example, the distances between the sensor point openings shown within dotted lines 254, 256, 258 and the center point of the stomal opening 18 may be in the range from 20 mm to 50 mm, e.g. in the range from 25 mm to 35 mm, such as about 30 mm.

In embodiments, the sensor point openings 254A, 254B, 256A, 256B, 258A, and 258B of the masking element 218 may be approximately oval in shape, that is, generally oblong, in an axial direction, and may vary in size, such as having a maximum dimension of between 1 mm and 3 mm, wherein such dimensions are equal to or less than the dimension of the corresponding sensor point openings in the first adhesive layer 200 (described below). Alternatively, each sensor point opening 254A, 254B, 256A, 256B, 258A, and 258B may possess a different shape in an axial direction other than being oval, such as being elliptical, round, polygonal, or possess at least one straight and at least one curved side or curved portion, such as a semicircle, wherein the foregoing shapes have a largest dimension that may vary in size, such as having a maximum dimension of between 1 mm and 3 mm, and wherein such dimensions are equal to or less than the dimension of the corresponding sensor point openings in the first adhesive layer 200. In embodiments, different sensor point openings of the masking element 218 may possess different shapes. In embodiments, different sensor point openings of the masking element 218 may possess different dimensions. In embodiments, different sensor point openings of the masking element 218 may possess different shapes, wherein one or more common-shaped sensor points may possess different dimensions.

While there are three sectors of sensor point openings, i.e., the sensor point openings in dotted lines 254, 256, 258, in alternative embodiments, there may be more or fewer sectors of sensor point openings. Additionally, or alternatively, more or fewer sensor points may be included in each of the dotted lines 254, 256, 258. Additionally or alternatively, while the primary sensor point openings shown within dotted line 254, secondary sensor point openings shown within dotted line 256, and tertiary sensor point openings shown within dotted line 258 are evenly distributed angularly about the stomal opening 18, in other embodiments, the primary sensor point openings shown within dotted line 254, secondary sensor point openings shown within dotted line 256, and tertiary sensor point openings shown within dotted line 258 may be unevenly distributed angularly about the stomal opening 18 and/or focused within an angular range about the stomal opening 18. Additionally or alternatively, while the illustrated embodiment depicts three sectors of sensor point openings (i.e., the primary sensor point openings, the secondary sensor point openings, and the tertiary sensor point openings), in alternative embodiments, the masking element 218 may include more or fewer sectors of sensor points openings. Additionally or alternatively, each sector may be unevenly distributed about the center point of the stomal opening 18, each sector may span different angular ranges, which may or may not be the same between the sectors, and/or may have different starting angles and/or different ending angles.

Figure 8:
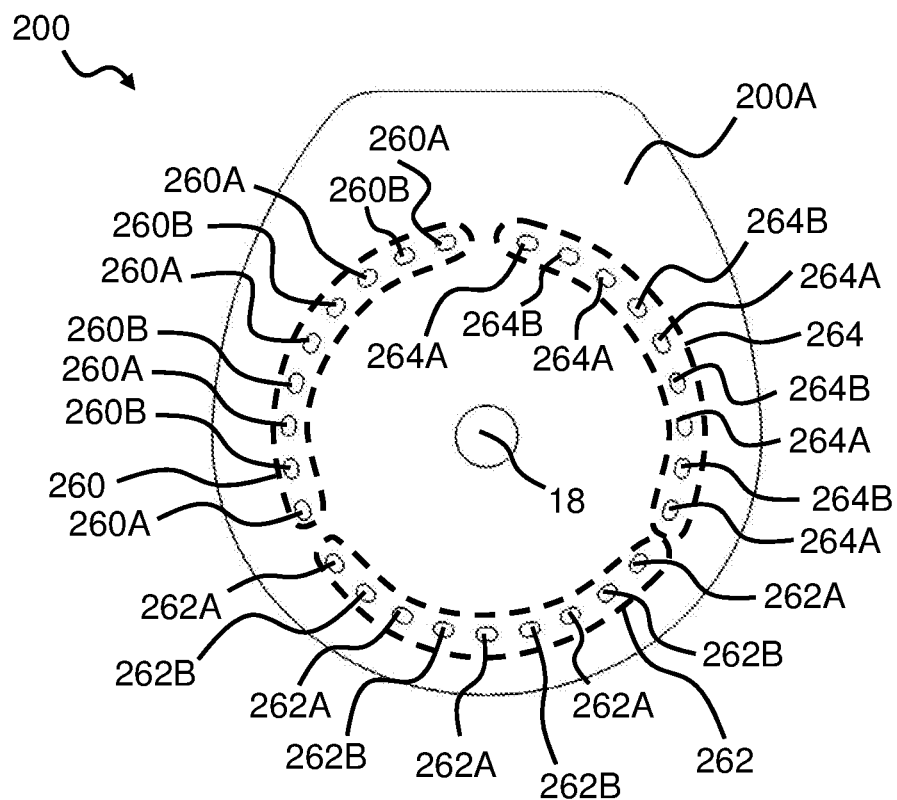
FIG. 8 is a distal view of an exemplary first adhesive layer.
Figure 9:
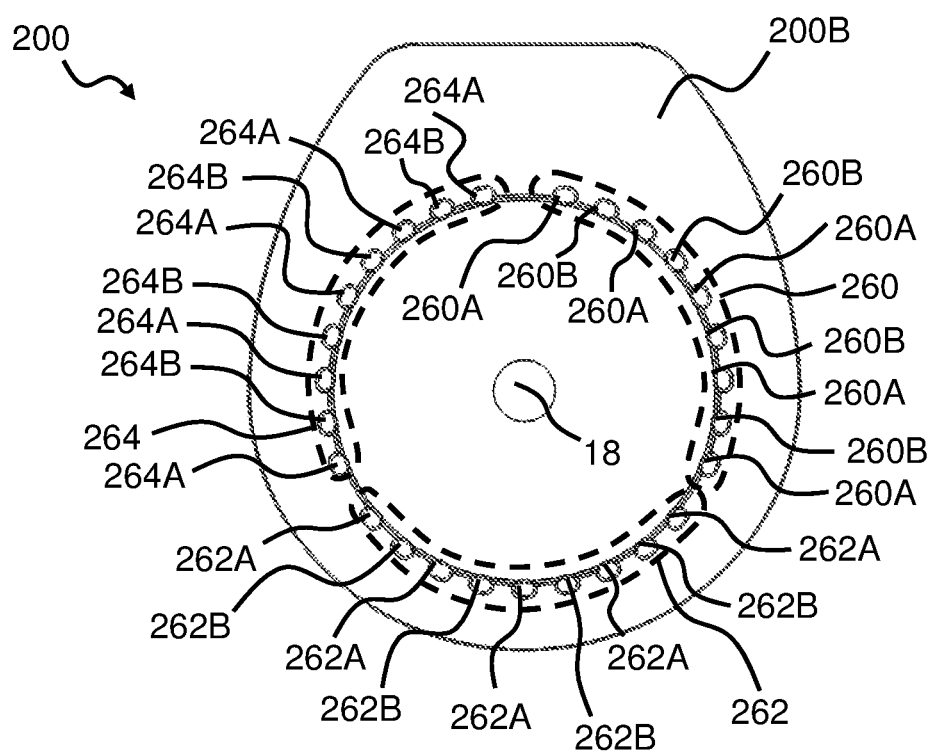
FIG. 9 is a proximal view of the first adhesive layer of FIG. 8.

FIG. 8 is a distal view of an exemplary first adhesive layer 200 and FIG. 9 is a proximal view of the first adhesive layer of FIG. 8. The first adhesive layer 200 has a plurality of sensor point openings. The sensor point openings of the first adhesive layer comprise primary sensor point openings shown within dotted line 260. Each primary sensor point opening is configured to overlap (that is, axially align with) a ground sensing part 222B of the fourth electrode part 240 that is electrically connected to the ground electrode 222 and/or a fourth sensing part 230B of the fourth electrode 230 of the electrode configuration 220. More particularly, the primary sensor point openings shown within dotted line 260 comprise, in the illustrated exemplary first adhesive layer 200, five primary first sensor point openings 260A each configured to overlap a ground sensing part 222B of the fourth electrode part 240 that is electrically connected to the ground electrode 222. In addition, the primary sensor point openings shown in dotted line 260 further comprise, in the illustrated exemplary first adhesive layer 200, four primary second sensor point openings 260B each configured to overlap a fourth sensing part 230B of the fourth electrode 230. In embodiments, each of the primary sensor point openings shown within dotted line 260 may be equal distances from a center point of the stomal opening 18. Alternatively, one or more of the primary sensor point openings shown within dotted line 260 may be different distances from a center point of the stomal opening 18. While the illustrated embodiment depicts five primary first sensor point openings 260A in the dotted line 260, in other embodiments, the first adhesive layer 200 includes more or fewer than five primary first sensor point openings 260A in the dotted line 260. Additionally or alternatively, while the illustrated embodiment depicts four primary second sensor point openings 260B in the dotted line 260, in other embodiments, the first adhesive layer 200 includes more or fewer than four primary second sensor point openings 260B in the dotted line 260.

Additionally or alternatively, the sensor point openings of the first adhesive layer 200 comprise secondary sensor point openings shown within dotted line 262. Each secondary sensor point opening is configured to overlap a fourth sensing part 230B of the fourth electrode 230 and/or a fifth sensing part 232B of the fifth electrode 232 of the electrode configuration 220. More particularly, the secondary sensor point openings shown within dotted line 262 comprise, in the illustrated exemplary first adhesive layer 200, five secondary first sensor point openings 262A each configured to overlap a fifth sensing part 232B of the fifth electrode 232. In addition, the secondary sensor point openings shown within dotted line 262 further comprise, in the illustrated exemplary first adhesive layer 200, four secondary second sensor point openings 262B each configured to overlap a fourth sensing part 230B of the fourth electrode 230. In embodiments, each of the secondary sensor point openings shown within dotted line 262 may be equal distances from a center point of the stomal opening 18. Alternatively, one or more of the secondary sensor point opening shown within dotted line 262 may be different distances from a center point of the stomal opening 18. In embodiments, the secondary sensor point openings shown within dotted line 262 may be substantially the same distance from a center point of the stomal opening 18 as the primary sensor point openings shown within dotted line 260. Alternatively, one or more of the secondary sensor point openings shown within dotted line 262 may be different distance(s) from a center point of the stomal opening 18 as one or more of the primary sensor point openings shown within dotted line 260. While the illustrated embodiment depicts five secondary first sensor point openings 262A in the dotted line 262, in other embodiments, the first adhesive layer 200 includes more or fewer than five secondary first sensor point openings 262A in the dotted line 262. Additionally or alternatively, while the illustrated embodiment depicts four secondary second sensor point openings 262B in the dotted line 262, in other embodiments, the first adhesive layer 200 includes more or fewer than four secondary second sensor point openings 262B in the dotted line 262.

Additionally or alternatively, the sensor point openings of the first adhesive layer 200 comprise tertiary sensor point openings shown within dotted line 264. Each tertiary sensor point opening is configured to overlap a fifth sensing part 232B of the fifth electrode 232 and/or a ground sensing part 222B of the fourth electrode part 240 that is electrically connected to the ground electrode 222 of the electrode configuration 220. More particularly, the tertiary sensor point openings shown within dotted line 264 comprise, in the illustrated exemplary first adhesive layer 200, five tertiary first sensor point openings 264A each configured to overlap a fifth sensing part 232B of the fifth electrode 232. In addition, the tertiary sensor point openings shown within dotted line 264 further comprise, in the illustrated exemplary first adhesive layer 200, four tertiary second sensor point openings 264B each configured to overlap a ground sensing part 222B of the fourth electrode part 240 that is electrically connected to the ground electrode 222. In embodiments, each of the tertiary sensor point openings shown within dotted line 264 may be equal distances from a center point of the stomal opening 18. Alternatively, one or more of the tertiary sensor point opening shown within dotted line 264 may be different distances from a center point of the stomal opening 18. In embodiments, the tertiary sensor point openings shown within dotted line 264 may be substantially the same distance from a center point of the stomal opening 18 as the primary sensor point openings shown within dotted line 260. Alternatively, one or more of the tertiary sensor point openings shown within dotted line 264 may be different distance(s) from a center point of the stomal opening 18 as one or more of the primary sensor point openings shown within dotted line 260. Additionally or alternatively, the tertiary sensor point openings shown within dotted line 264 may be substantially the same distance from a center point of the stomal opening 18 as the secondary sensor point openings shown within dotted line 262. Alternatively, one or more of the tertiary sensor point openings shown within dotted line 264 may be different distance(s) from a center point of the stomal opening 18 as one or more of the secondary sensor point openings shown within dotted line 262. While the illustrated embodiment depicts five tertiary first sensor point openings 264A in the dotted line 264, in other embodiments, the first adhesive layer 200 includes more or fewer than five tertiary first sensor point openings 264A in the dotted line 264. Additionally or alternatively, while the illustrated embodiment depicts four tertiary second sensor point openings 264B in the dotted line 264, in other embodiments, the first adhesive layer 200 includes more or fewer than four tertiary second sensor point openings 264B in the dotted line 264.

In embodiments, the distance between neighbouring sensor point openings shown within dotted lines 260, 262, 264 may be uniform or non-uniform. Additionally or alternatively, a range of distances may separate neighbouring sensor point openings shown within dotted lines 260, 262, 264. For example, the distances between neighbouring sensor point openings shown within dotted lines 260, 262, 264 may be approximately 2 mm-2.5 mm. Additionally or alternatively, the distance between a sensor point opening shown within dotted lines 260, 262, 264 and the center point of the stomal opening 18 may be the same for each sensor point opening shown within dotted lines 260, 262, 264 or be different for different sensor point openings shown within dotted lines 260, 262, 264. Additionally or alternatively, a range of distances may separate the sensor point openings shown within dotted lines 260, 262, 264 from the center point of the stomal opening 18. For example, the distances between the sensor point openings shown within dotted lines 260, 262, 264 and the center point of the stomal opening 18 may be in the range from 20 mm to 50 mm, e.g. in the range from 25 mm to 35 mm, such as about 30 mm.

Additionally or alternatively, while the illustrated embodiment depicts three sectors of sensor point openings (i.e., the primary sensor point openings, the secondary sensor point openings, and the tertiary sensor point openings), in alternative embodiments, the first adhesive layer 200 may include more or fewer sectors of sensor points openings. Additionally or alternatively, each sector may be unevenly distributed about the center point of the stomal opening 18, each sector may span different angular ranges, which may or may not be the same between the sectors, and/or may have different starting angles and/or different ending angles.

In embodiments, the sensor point openings 260A, 260B, 262A, 262B, 264A, and 264B of the first adhesive layer 200 may be approximately oval in shape, that is, generally oblong, in an axial direction, and may vary in size, such as having a maximum dimension of between 1 mm and 3 mm. Alternatively, each sensor point opening 260A, 260B, 262A, 262B, 264A, and 264B of the first adhesive layer 200 may possess a different shape in an axial direction other than being oval, such as being elliptical, round, polygonal, or possess at least one straight side and at least one curved side or curved portion, such as a semicircle, wherein the foregoing shapes have a largest dimension that may vary in size, such as having a maximum dimension of between 1 mm and 3 mm. In embodiments, different sensor point openings of the first adhesive layer 200 may possess different shapes. In embodiments, different sensor point openings of the first adhesive layer 200 may possess different dimensions. In embodiments, different sensor point openings of the first adhesive layer 200 may possess different shapes, wherein one or more common-shaped sensor points may possess different dimensions.

In view of the foregoing, the primary sensor point openings shown within dotted line 254 of the masking element 218 (illustrated in FIG. 7) may overlap the primary sensor point openings shown within dotted line 260 of the first adhesive layer 200 (illustrated in FIG. 8). More specifically, each of the five primary first sensor point openings 254A may overlap a respective one of the five primary first sensor point openings 260A. As such, the ground sensor part 222B, which the five primary first sensor point openings 254A and the five primary first sensor point openings 260A overlap, may be exposed in an axial direction from the proximal surface 200B of the first adhesive layer 200. Furthermore, each of the four primary second sensor point openings 254B may overlap a respective one of the four primary second sensor point openings 260B. As such, the fourth sensor part 230B, which the four primary second sensor point openings 254B and the four primary second sensor point openings 260B overlap, may be exposed in an axial direction from the proximal surface 200B of the first adhesive layer 200. In embodiments, when output spans or bridges from a ground sensor part 222B to a fourth sensor part 230B, a leak may be detected by, for example, the monitor device 6. More specifically, a drop in resistance may be sensed between a ground sensor part 222B and a fourth sensor part 230B by the monitor device 6 in response to output spanning and/or bridging from a ground sensor part 222B to a fourth sensor part 230B.

Additionally or alternatively, the second sensor point openings shown within dotted line 256 of the masking element 218 (illustrated in FIG. 7) may overlap the second sensor point openings shown within dotted line 262 of the first adhesive layer 200 (illustrated in FIG. 8). More specifically, each of the five secondary first sensor point openings 256A may overlap a respective one of the five secondary first sensor point openings 262A. As such, the fifth sensor part 232B, which the five secondary first sensor point openings 256A and the five secondary first sensor point openings 262A overlap, may be exposed in an axial direction from the proximal surface 200B of the first adhesive layer 200. Furthermore, each of the four secondary second sensor point openings 256B may overlap a respective one of the four secondary second sensor point openings 262B. As such, the fourth sensor part 230B, which the four secondary second sensor point openings 256B and the four secondary second sensor point openings 262B overlap, may be exposed in an axial direction from the proximal surface 200B of the first adhesive layer 200. In embodiments, when output spans or bridges from a fifth sensor part 232B to a fourth sensor part 230B, a leak may be detected by, for example, the monitor device 6. More specifically, a drop in resistance may be sensed between a fifth sensor part 232B and a fourth sensor part 230B by the monitor device 6 in response to output spanning and/or bridging from a fifth sensor part 232B to a fourth sensor part 230B.

Additionally or alternatively, the tertiary sensor point openings shown within dotted line 258 of the masking element 218 (illustrated in FIG. 7) may overlap the tertiary sensor point openings shown within dotted line 264 of the first adhesive layer 200 (illustrated in FIG. 8). More specifically, each of the five tertiary first sensor point openings 258A may overlap a respective one of the five tertiary first sensor point openings 264A. As such, the ground sensor part 222B, which the five tertiary first sensor point openings 258A and the five tertiary first sensor point openings 264A overlap, may be exposed in an axial direction from the proximal surface 200B of the first adhesive layer 200. Furthermore, each of the four tertiary second sensor point openings 258B may overlap a respective one of the four tertiary second sensor point openings 264B. As such, the fifth sensor part 232B, which the four tertiary second sensor point openings 258B and the four tertiary second sensor point openings 264B overlap, may be exposed in an axial direction from the proximal surface 200B of the first adhesive layer 200. In embodiments, when output spans or bridges from a ground sensor part 222B to a fifth sensor part 232B, a leak may be detected by, for example, the monitor device 6. More specifically, a drop in resistance may be sensed between a ground sensor part 222B and a fifth sensor part 232B by the monitor device 6 in response to output spanning and/or bridging from a ground sensor part 222B to a fifth sensor part 232B.

In view of the foregoing, and as those skilled in the art will appreciate, a base plate 4 and/or the sensor assembly part 700 may include a configuration for detecting leakage associated with use of an ostomy appliance. More particularly, a base plate 4 and/or the sensor assembly part 700 may include a first adhesive layer 200 and a plurality of electrodes, such as at least two electrodes, that are located distally of the first adhesive layer, wherein the configuration of the first adhesive layer 200 relative to the electrodes provides leak detection monitoring locations. A first opening of at least two openings in the first adhesive layer overlaps a portion of a first electrode of the plurality of electrodes and a second opening of the at least two openings in the first adhesive layer overlaps a portion of a second electrode of the plurality of electrodes. Although additional openings can be provided, by providing at least two openings in the first adhesive layer a leak may be detected when output spans or bridges the two openings to essentially complete the circuit between the two electrodes.

In accordance with at least one embodiment, a base plate and/or a sensor assembly part for an ostomy appliance including selective sensor points is provided for detecting a leak. More particularly, and referring again to FIG. 8, the base plate and/or the sensor assembly part includes a first adhesive layer 200 with a stomal opening 18 having a center point. In addition, the first adhesive layer includes a proximal surface configured to be attached to the skin surface of a user, and further includes a plurality of sensor point openings 260A, 260B, 262A, 262B, 264A and 264B arranged circumferentially around the center point. For the embodiment shown in FIG. 8, the various sensor point openings 260A, 260B, 262A, 262B, 264A and 264B are located at a substantially constant radial distance from the center point of the stomal opening 18. However, the various sensor point openings 260A, 260B, 262A, 262B, 264A and 264B could be positioned at more than one radial distance from the center point of the stomal opening 18; that is, at least one sensor point opening 260A, 260B, 262A, 262B, 264A and 264B may be closer to the center point of the stomal opening 18 than another of the sensor point openings 260A, 260B, 262A, 262B, 264A and 264B.

With reference again to FIG. 6, an embodiment of the base plate and/or the sensor assembly part further includes a plurality of electrodes for detecting a leak, such as the fourth electrode 230, the fifth electrode 232 and the fourth electrode part 240 (wherein the fourth electrode part 240 is electrically connected to the ground electrode 222). The plurality of electrodes are preferably located distally of the first adhesive layer 200. Although the plurality of electrodes may include all three of the fourth electrode 230, the fifth electrode 232 and the fourth electrode part 240, subcombinations of the foregoing electrodes may be provided as an embodiment of the base plate and/or the sensor assembly part. More particularly, in a least one embodiment, the plurality of electrodes includes the fourth electrode 230 and the fourth electrode part 240. In another embodiment, the plurality of electrodes includes the fourth electrode 230 and the fifth electrode 232. In yet another embodiment, the plurality of electrodes includes the fifth electrode 232 and the fourth electrode part 240.

Preferably, the fourth electrode 230 includes fourth sensing parts 230B, the fifth electrode includes fifth sensing parts 232B, and the fourth electrode part 240 includes ground sensing parts 222B. The fourth sensing parts 230B, fifth sensing parts 232B, and ground sensing parts 222B are locations along their respective electrodes for detecting output from the ostomy appliance. Accordingly, the fourth sensing parts 230B, fifth sensing parts 232B and ground sensing parts 222B may optionally be structurally modified from the adjacent portions of their respective electrodes. By way of non-limiting example, one or more of the fourth sensing parts 230B, fifth sensing parts 232B and ground sensing parts 222B may optionally be wider than the conductor parts of the electrodes with which they are associated.

In at least one embodiment, at least a first sensor point opening in the first adhesive layer overlaps a portion of a first electrode located distally of the first adhesive layer 200, and at least a second sensor point opening in the first adhesive layer overlaps a portion of a second electrode located distally of the first adhesive layer 200. With regard to the location of the electrodes relative to the first adhesive layer 200, in at least one embodiment the electrodes may be located such that another layer of material is positioned between the first adhesive layer 200 and the electrodes. With regard to the location of the sensor point openings, the first sensor point opening overlaps one of the fourth sensing parts 230B of the fourth electrode 230, or one of the fifth sensing parts 232B of the fifth electrode 232, or one of the ground sensing parts 222B of the fourth electrode part 240 associated with the ground electrode 222. In addition, the second sensor point overlaps one of the fourth sensing parts 230B of the fourth electrode 230, or one of the fifth sensing parts 232B of the fifth electrode 232, or one of the ground sensing parts 222B of the fourth electrode part 240 associated with the ground electrode 222. However, for an embodiment that only includes two sensor point openings, the second sensor point opening will overlap a sensing part associated with a different electrode than the sensing part associated with the first sensing point opening. Accordingly, if the first sensing point opening overlaps a fourth sensing part 230B, then the second sensing point opening overlaps one of either the fifth sensing parts 232B or the ground sensing parts 222B; if the first sensing point opening overlaps a fifth sensing part 232B, then the second sensing point opening overlaps one of either the fourth sensing parts 230B or the ground sensing parts 222B; and if the first sensing point opening overlaps a ground sensing part 222B, then the second sensing point opening overlaps one of either the fourth sensing parts 230B or the fifth sensing parts 232B.

In at least one embodiment, at least one primary first sensor point opening 260A overlaps a portion of the fourth electrode part 240, and at least one primary second sensor point opening 260B overlaps a portion of the fourth electrode 230. Alternatively, in at least one embodiment, at least one secondary first sensor point opening 262A overlaps a portion of the fifth electrode 232, and at least one secondary second sensor point opening 262B overlaps a portion of the fourth electrode 230. Alternatively yet, in at least one embodiment, at least one tertiary first sensor point opening 264A overlaps a portion of the fifth electrode part 232, and at least one tertiary second sensor point opening 264B overlaps a portion of the fourth electrode part 240. Moreover, as those skilled in the art will appreciate, more than two sensor point openings may be present in the first adhesive layer, including 3, 4, 5, 6, 7, 8, 9, 10, 11, 12, 13, 14, 15, 16, 17, 18, 19, 20, 21, 22, 23, 24, 25, 26, 27, or more sensor point openings. Such sensor point openings may be arranged angularly around the stomal opening 18 so that leak detection monitoring is distributed around the stomal opening 18, or alternatively, the sensor point openings may be localized or focused angularly around the stomal opening 18. As depicted in the embodiment shown in FIG. 8, first, second and third regions of sensor point openings can be provided, such as to provide primary sensor point openings, secondary sensor point openings and tertiary sensor point openings, respectively.

With reference again to FIGS. 3 and 4, in at least one embodiment, in addition to a first adhesive layer 200 and a plurality of electrodes 216, the base plate 4 and/or the sensor assembly part 700 may include a second adhesive layer 202, wherein the second adhesive layer 202 is located distally of the first adhesive layer 200 and the plurality of electrodes 216. In at least one embodiment, in addition to a first adhesive layer 200 and a plurality of electrodes 216, the base plate 4 and/or the sensor assembly part 700 may include a masking element 218, wherein the masking element 4 is arranged between the second adhesive layer 202 and the first adhesive layer 200. In at least one embodiment, the masking element 218 is more insulative than the first adhesive layer 200. In at least one embodiment, the masking element 218 includes a plurality of sensor point openings, such as a plurality of sensor point openings 254A, 254B, 256A, 256B, 258A and 258B depicted in FIG. 7. In at least one embodiment, at least two sensor point openings in the masking element 218, such as at least two of sensor point openings 254A, 254B, 256A, 256B, 258A and 258B shown in FIG. 7, align with the sensor point openings in the first adhesive layer 200, such as at least two of sensor point openings 260A, 260B, 262A, 262B, 264A and 264B shown in FIG. 8, and further align with at least a portion of one of the fourth electrode 230, the fifth electrode 232 and the fourth electrode part 240, to form a sensor point. In addition, in at least one embodiment, each sensor point opening of the first adhesive layer 260A, 260B, 262A, 262B, 264A and 264B aligns with a corresponding sensor point opening of the masking element 254A, 254B, 256A, 256B, 258A and 258B, and further align with at least a portion of one of the fourth electrode 230, the fifth electrode 232 and the fourth electrode part 240, to form a sensor point.

In at least one embodiment, the diameters of the sensor point openings 260A, 260B, 262A, 262B, 264A and 264B of the first adhesive layer 200 are larger than diameters of the sensor point openings 254A, 254B, 256A, 256B, 258A and 258B of the masking element 218. In at least one embodiment, and as depicted in FIG. 7, the masking element 218 has twenty-seven sensor point openings 254A, 254B, 256A, 256B, 258A and 258B. In addition, as depicted in FIG. 8, in at least one embodiment the first adhesive layer 200 has twenty-seven sensor point openings 260A, 260B, 262A, 262B, 264A and 264B, and the base plate 4 and/or the sensor assembly part 700 has twenty-seven sensor points. In at least one embodiment, each sensor point has a diameter greater than one millimeter (e.g., 1.0 mm-4.0 mm).

Referring again to FIGS. 6-8, and in accordance with at least one embodiment, the plurality of electrodes 216 are configured to form a plurality of sensing sectors, such as a bottom sensing sector and lateral sensing sectors located on either side of the bottom sensing sector. However, as those skilled in the art will appreciate, a single sensing sector could be provided, or alternatively, two sensing sectors could be provided, or alternatively yet, greater than three sensing sectors could be provided, such as 4, 5, 6 or more sensing sectors, with an appropriate number of electrodes situated to accommodate the desired number of sensing sectors. For the exemplary embodiment depicted in FIGS. 6-8 wherein three sensing sectors are illustrated, two electrodes of the plurality of electrodes form each sensing sector. More particularly, a bottom sensing sector includes the fourth electrode 230 and the fifth electrode 232, and the two laterally situated sensing sectors include the fourth electrode 230 and the fourth electrode part 240 of the ground electrode 222, and the fifth electrode 232 and the fourth electrode part 240 of the ground electrode 222. Accordingly, each electrode of the plurality of electrodes is used to form two sensing sectors of the plurality of sensing sectors. That is, as shown in FIG. 6, the fourth electrode 230 is used in two sensing sectors, the fifth electrode 232 is used in two sensing sectors, and the fourth electrode part 240 of the ground electrode 222 is used in two sensing sectors.

Although not required, advantageously, because of their staggered configuration the sensing parts of each electrode are configured, for the exemplary embodiment shown in FIG. 6, to be substantially equidistant radially from the center point of the stomal opening 18. Accordingly, travel distances for a leaking fluid material are substantially equal to neighbouring sensing parts of two different electrodes, that is, two of either the fourth electrode 230, the fifth electrode 232 or the fourth electrode part 240 of the ground electrode 222. In at least one embodiment, the plurality of sensor point openings 260A, 260B, 262A, 262B, 264A and 264B are generally oval shape as viewed in an axial direction. In addition, the plurality of sensor point openings 260A, 260B, 262A, 262B, 264A and 264B may extend through the first adhesive layer 200. Similarly, the sensor point openings 254A, 254B, 256A, 256B, 258A and 258B of the masking element 218 may extend through the masking element.

The sensor point openings and electrode positions are configured to provide a warning to the user (such as described herein, and which may include, but is not limited to one or more of a tactile warning, alert via a mobile phone and/or a wearable device such as a wrist band or watch) that a leak may occur, thereby allowing the user to take action to prevent a leak or otherwise mitigate the undesirable results of a leak adjacent the user's stoma and associated with the ostomy appliance. Accordingly, a leak, as measured by a change in resistance between the electrodes included in the bottom sensing sector and/or one of the two lateral sensing sectors (as illustrated in FIG. 8), may be sensed by, for example, the monitor device 6 (depicted in FIG. 1). When the resistance between two of the fourth electrode 230, the fifth electrode 232, and the fourth electrode part 240 of the ground electrode 222 decreases below a threshold level, the monitor device 6 may send an indication to the user that a leak is predicted, thereby allowing the user to take action, such as the monitor device 6 may send a signal to the user suggesting the user change his/her ostomy appliance 2 and/or base plate 4.

Figure 10:
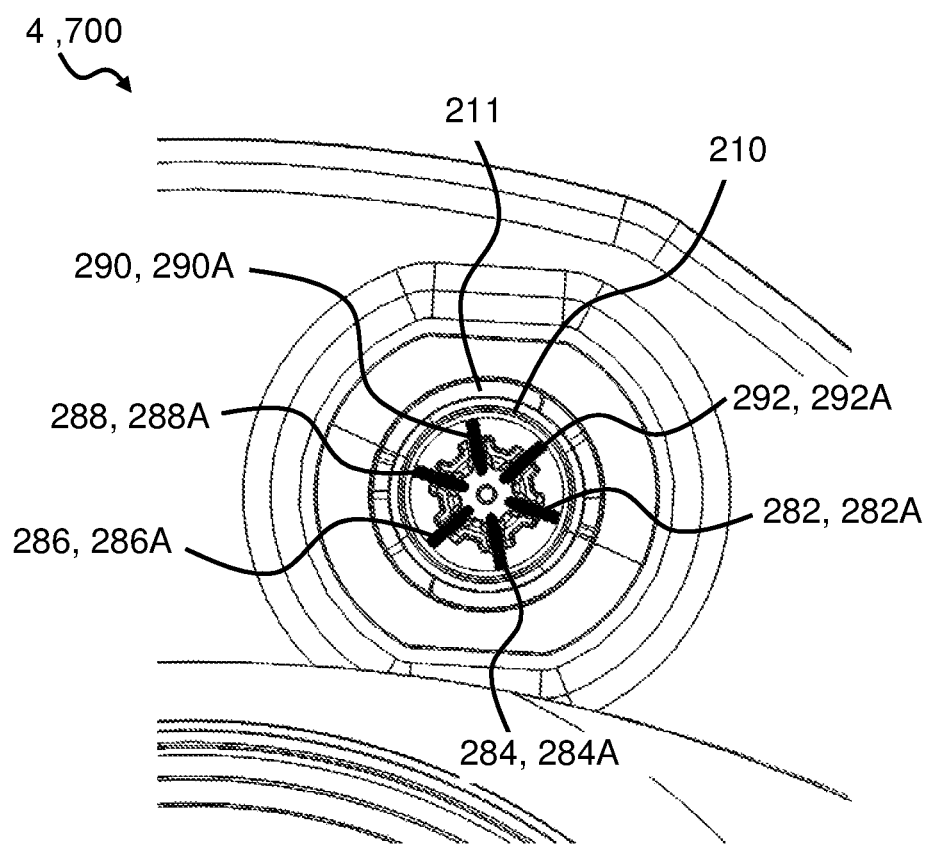
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate and/or the sensor assembly part and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284A, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or the sensor assembly part, the number of terminals, and the position of the terminals in the coupling part may be adapted to the electrode configuration used in the electrode assembly of the base plate and/or the sensor assembly part.

Figure 11A:
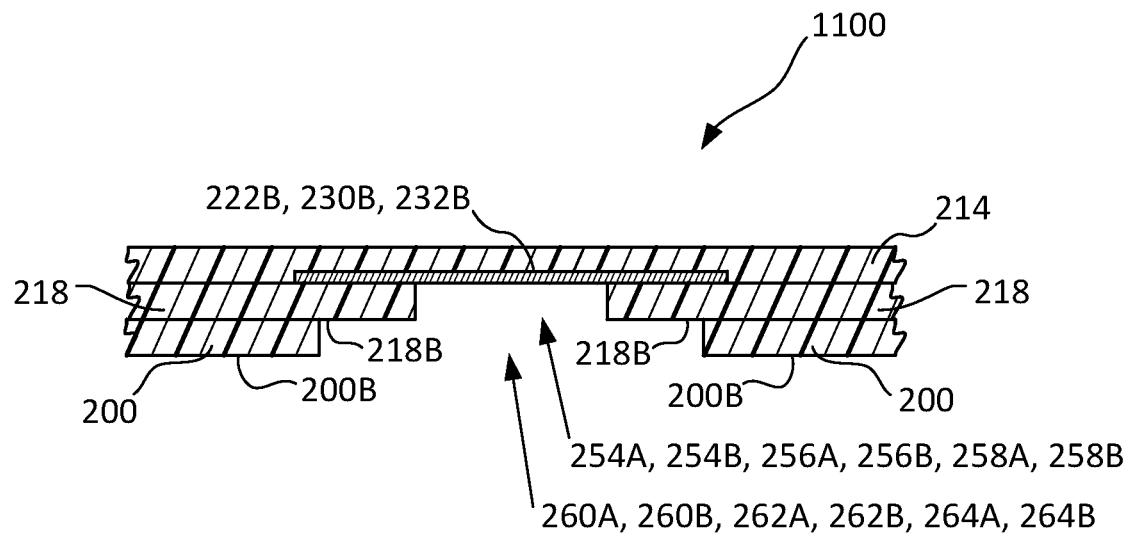
FIGS. 11A and 11B are cross-sectional views of a sensor point opening without a filling material and with a filling material, respectively.

Referring now to FIG. 11A, a cross section of a portion 1100 of the base plate and/or the sensor assembly part is shown, wherein a sensing point is illustrated. For the embodiment depicted in FIG. 11A, the sensing point opening in the first adhesive layer 200 can be seen to align axially with the sensing point opening in the masking element 218, such that a portion of the sensing part 222B, 230B, 232B is exposed.

In embodiments, the sensor parts 222B, 230B, 232B of the fourth electrode part 240, fourth electrode 230 and fifth electrode 232, respectively, may be approximately oval in shape, that is, generally oblong, in an axial direction, and may vary in size, such as having a maximum dimension of between 1 mm and 3 mm, wherein such dimensions are approximately equal to, less than, or greater than the dimension of the corresponding sensor point openings in the masking element 218. Alternatively, each of the sensing parts 222B, 230B and 232B may possess a different shape in an axial direction other than being oval, such as being elliptical, round, polygonal, or possess at least one straight side and at least one curved side or curved portion, such as a semicircle, wherein the foregoing shapes have a largest dimension that may vary in size, such as having a maximum dimension of between 1 mm and 3 mm, and wherein such dimensions are approximately equal to, less than, or greater than the dimension of the corresponding sensor point openings in the masking element 218. In embodiments, different sensing parts may possess different shapes. In embodiments, different sensing parts may possess different dimensions. In embodiments, different sensing parts may possess different shapes, wherein one or more common-shaped sensing parts may possess different dimensions.

Figure 11B:
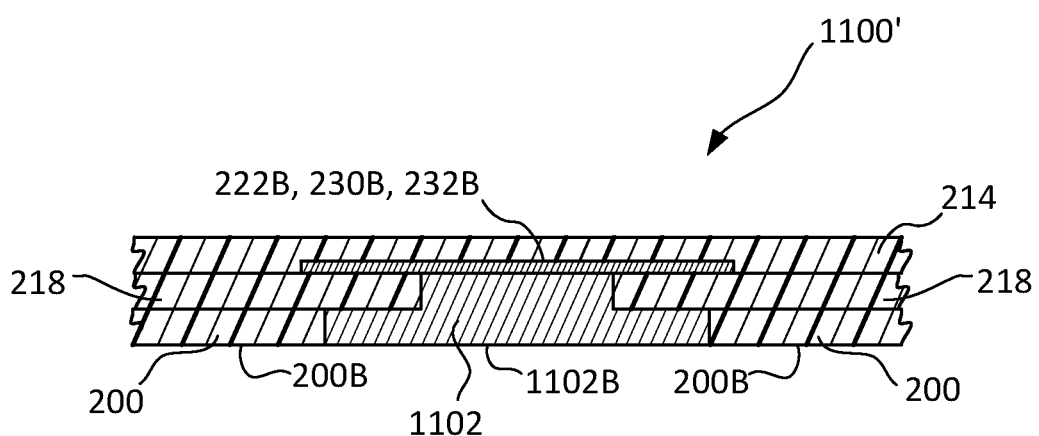

Referring now to FIG. 11B, a modified portion 1100' of a base plate and/or the sensor assembly part is shown. More particularly, in at least one embodiment, a filling material 1102 is disposed in the sensor point and/or is otherwise situated adjacent at least a portion of the sensing part of the fourth electrode 230, fifth electrode 232 and fourth electrode part 240 (connected to the ground electrode 222) associated with sensor point openings 260A, 260B, 262A, 262B, 264A and 264B of the first adhesive layer 200, and sensor point openings 254A, 254B, 256A, 256B, 258A and 258B of the masking element 218. In embodiments, the filling material 1102 may include a proximal surface 1102B that is substantially level with adjacent portions of the proximal surface 200B of the first adhesive layer 200. Alternatively, the filling material 1102 may have a proximal surface 1102B that is not level with adjacent portions of the proximal surface 200B of the first adhesive layer 200. In embodiments, the filling material 1102 is preferably a structurally supportive material to maintain the sensing point pathway to the sensing part 222B, 230B, 232B, such as when the base plate 4 and/or the sensor assembly part 700 is packaged and/or is being transported.

Figure 12:
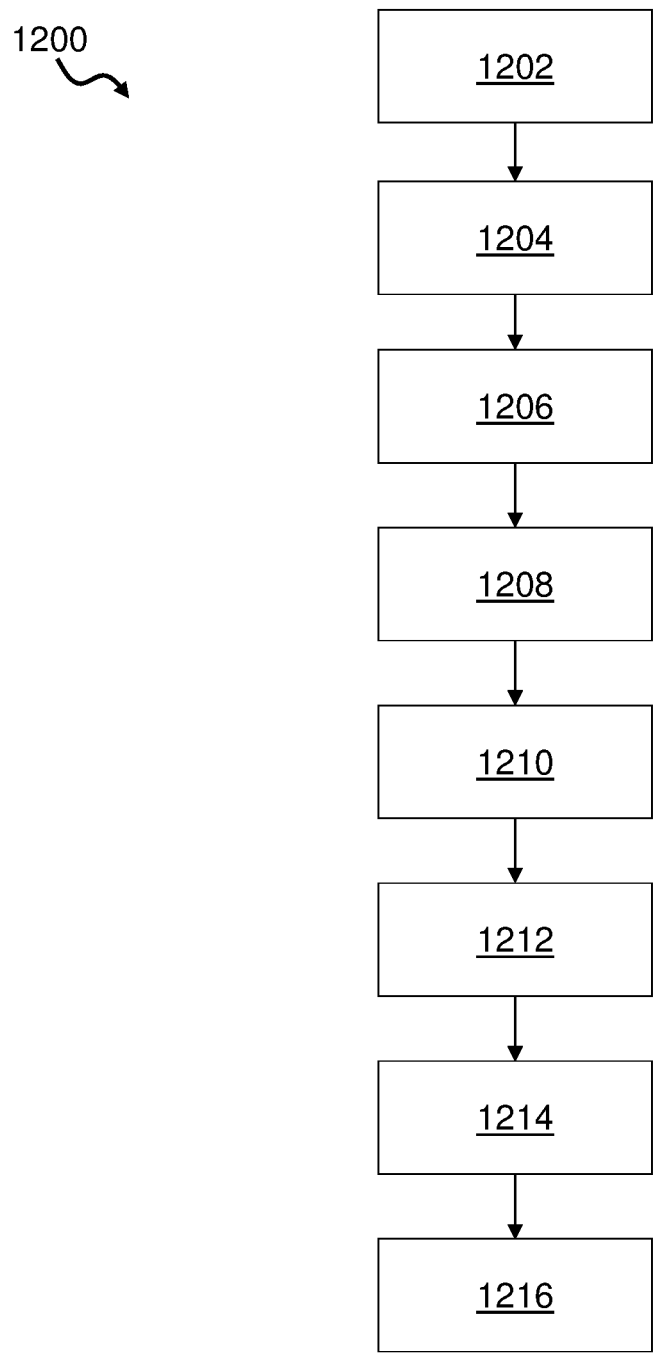
FIG. 12 illustrates a flow diagram of a method of manufacturing a base plate and/or sensor assembly part of an ostomy appliance with selective sensor points.

Methods of manufacturing a base plate and/or a sensor assembly part of an ostomy appliance with selective sensor points are also contemplated. More particularly, FIG. 12 shows a flow diagram of an exemplary method for manufacturing 1200 a base plate 4 and/or a sensor assembly part for an ostomy appliance 2 including selective sensor points to form a leak sensor, such as a base plate 4 and/or a sensor assembly part as disclosed in the previous figures. For illustrations of the structural features of the base plate 4 and/or the sensor assembly part, reference is made to the other figures, in particular FIGS. 3, 6, 7 and 8.

Referring still to FIG. 12, the method 1200 includes forming 1202 a first adhesive layer 200 comprising: a stomal opening 18 with a center point, a proximal surface 200B configured to be attached to a skin surface of a user, and a plurality of sensor point openings (such as at least two of: 260A, 260B, 262A, 262B, 264A and 264B) arranged circumferentially around the center point at respective radial distances. The method of manufacturing 1200 further includes arranging 1204 a plurality of electrodes (such as at least two of: fourth electrode 230, fifth electrode 232, and the fourth electrode part 240 of the ground electrode 222) distally of the first adhesive layer 200, the plurality of electrodes comprising a first leakage electrode and a second leakage electrode, a sensing part of the first leakage electrode aligning with a first sensor point opening of the plurality of sensor point openings and a sensing part of the second leakage electrode aligning with a second sensor point opening of the plurality of sensor point openings to form a leak sensor.

The method of manufacturing 1200 may further include positioning 1206 a second adhesive layer 202 distally of the first adhesive layer 200, the plurality of electrodes (such as at least two of: fourth electrode 230, fifth electrode 232, and the fourth electrode part 240 of the ground electrode 222) being located between the first adhesive layer 200 and the second adhesive layer 202.

The method of manufacturing 1200 may further include arranging 1208 a masking element 218 between the second adhesive layer 202 and the first adhesive layer 200. The masking element 218 may be more insulative than the first adhesive layer 200.

The method of manufacturing 1200 may still further include forming 1210 the masking element 218, wherein the masking element 218 includes a second plurality of sensor point openings (such as at least two of: 254A, 254B, 256A, 256B, 258A and 258B); and arranging the masking element 218 between the second adhesive layer 202 and the first adhesive layer 200, which includes substantially aligning each opening of the second plurality of sensor point openings (the at least two of: 254A, 254B, 256A, 256B, 258A and 258B) with an opening of the plurality of sensor point openings (at least two of: 260A, 260B, 262A, 262B, 264A and 264B).

The method of manufacturing 1200 may yet further include positioning 1212 the sensor point openings (at least two of: 260A, 260B, 262A, 262B, 264A and 264B) substantially equidistant radially from the center point of the stomal opening 18.

The method of manufacturing 1200 may still further include forming 1214 the plurality of sensor point openings (the at least two of: 260A, 260B, 262A, 262B, 264A and 264B) to extend through the first adhesive layer 200. The method of manufacturing 1200 may also include forming 1216 the sensor point openings (the at least two of: 254A, 254B, 256A, 256B, 258A and 258B) of the masking element 218 to extend through the masking element 218.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments of the present disclosure are set out in the following items:

1. A sensor assembly part for an ostomy appliance including selective sensor points, the sensor assembly part comprising:
   a first adhesive layer comprising: a stomal opening with a center point, a proximal surface configured to be attached to a skin surface of a user, and a plurality of sensor point openings arranged circumferentially around the center point at respective radial distances; and
   a plurality of electrodes located distally of the first adhesive layer, the plurality of electrodes comprising a first leakage electrode and a second leakage electrode, a sensing part of the first leakage electrode aligning with a first sensor point opening of the plurality of sensor point openings of the first adhesive layer and a sensing part of the second leakage electrode aligning with a second sensor point opening of the plurality of sensor point openings of the first adhesive layer to form a leak sensor.

2. The sensor assembly part of item 1, further comprising a masking element, the masking element being arranged between a second adhesive layer and the first adhesive layer, the masking element being more insulative than the first adhesive layer.

3. The sensor assembly part of item 2, the masking element comprising a plurality of sensor point openings, each sensor point opening of the first adhesive layer aligning with a sensor point opening of the masking element to form a sensor point.

4. The sensor assembly part of item 3, further comprising a filling material disposed in each sensor point.

5. The sensor assembly part of any of items 3 and 4, wherein diameters of the sensor point openings of the first adhesive layer are larger than diameters of the sensor point openings of the masking element.

6. The sensor assembly part of any of items 1-5, the plurality of electrodes forming a plurality of sensing sectors, wherein two electrodes of the plurality of electrodes form each sensing sector.

7. The sensor assembly part of any of items 1-6, each electrode of the plurality of electrodes being used to form two sensing sectors of the plurality of sensing sectors.

8. The sensor assembly part of any of items 1-7, the plurality of sensor point openings extending through the first adhesive layer.

9. The sensor assembly part of any of items 3-8, the second plurality of sensor point openings extending through the masking element.

10. The sensor assembly part of any of items 1-9, the respective radial distances being generally equal distances from the center point.

11. The sensor assembly part of any of items 1-10, the plurality of sensor point openings comprising a generally oval shape as viewed in an axial direction.

12. A method of manufacturing a sensor assembly part of an ostomy appliance with selective sensor points, the method comprising:
   forming a first adhesive layer comprising: a stomal opening with a center point, a proximal surface configured to be attached to a skin surface of a user, and a plurality of sensor point openings arranged circumferentially around the center point at respective radial distances; and
   arranging a plurality of electrodes distally of the first adhesive layer, the plurality of electrodes comprising a first leakage electrode and a second leakage electrode, a sensing part of the first leakage electrode aligning with a first sensor point opening of the plurality of sensor point openings and a sensing part of the second leakage electrode aligning with a second sensor point opening of the plurality of sensor point openings to form a leak sensor.

13. The method of item 12, further comprising positioning a second adhesive layer distally of the first adhesive layer, the plurality of electrodes being located between the first adhesive layer and the second adhesive layer.

14. The method of item 12, further comprising arranging a masking element between the second adhesive layer and the first adhesive layer, the masking element being more insulative than the first adhesive layer.

15. The method of item 14, further comprising:
   forming the masking element, the masking element comprising a second plurality of sensor point openings; and
   wherein arranging the masking element between the second part and the first adhesive layer comprises aligning each opening of the second plurality of sensor point openings with an opening of the plurality of sensor point openings.

16. The method of item 15, the second plurality of sensor point openings extending through the masking element.

17. The method of any of items 12-16, the respective radial distances being generally equal distances from the center point.

18. The method of any of items 12-17, the plurality of sensor point openings extending through the first adhesive layer.

LIST OF REFERENCES 1 ostomy system
2 ostomy appliance
4 base plate
6 monitor device
8 accessory device
10 server device
12 network
14 coupling member
16 coupling ring
18 stomal opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly 214A distal surface of support layer
214B proximal surface of support layer
216 electrodes of electrode assembly
218 masking element
218A distal surface of masking element
218B proximal surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
700 sensor assembly part
1100 portion of base plate
1100' modified portion of base plate with filling material in sensor point opening
1102 filling material in sensor point opening
1102B proximal surface of filling material in sensor point opening
1200 method of manufacturing a base plate of an ostomy appliance with selective sensor points
1202 forming a first adhesive layer
1204 arranging a plurality of electrodes
1206 positioning a second adhesive layer
1208 arranging a masking element
1210 forming the masking element
1212 positioning the sensor point openings equidistant radially
1214 forming the sensor point openings of the first adhesive layer to extend through the first adhesive layer
1216 forming the sensor point openings of the masking element to extend through the masking element

The invention claimed is:

1. A base plate for a medical appliance including selective sensor points, the base plate comprising:
a first adhesive layer comprising:
a stomal opening with a center point;
a proximal surface configured to be attached to a skin surface of a user; and
a plurality of sensor point openings arranged circumferentially around the center point at respective radial distances; and
a plurality of electrodes located distally of the first adhesive layer, the plurality of electrodes comprising:
a first leakage electrode and a second leakage electrode;
a sensing part of the first leakage electrode aligning with a first sensor point opening of the plurality of sensor point openings of the first adhesive layer, and
a sensing part of the second leakage electrode aligning with a second sensor point opening of the plurality of sensor point openings of the first adhesive layer to form a leak sensor;
wherein each of the plurality of sensor point openings extends through the first adhesive layer from the proximal surface to a distal surface of the first adhesive layer, thereby exposing sensing parts of the plurality of electrodes.

2. The base plate of claim 1, further comprising a masking element, the masking element being arranged between a second adhesive layer and the first adhesive layer, the masking element being more insulative than the first adhesive layer.

3. The base plate of claim 2, the masking element comprising a plurality of sensor point openings, each sensor point opening of the first adhesive layer aligning with a sensor point opening of the masking element to form a sensor point.

4. The base plate of claim 3, further comprising a filling material disposed in each sensor point.

5. The base plate of claim 3, wherein diameters of the sensor point openings of the first adhesive layer are larger than diameters of the sensor point openings of the masking element.

6. The base plate of claim 1, the plurality of electrodes forming a plurality of sensing sectors, wherein two electrodes of the plurality of electrodes form each sensing sector.

7. The base plate of claim 1, each electrode of the plurality of electrodes being used to form two sensing sectors of the plurality of sensing sectors.

8. The base plate of claim 3, the second plurality of sensor point openings extending through the masking element.

9. The base plate of claim 1, the respective radial distances being generally equal distances from the center point.

10. The base plate of claim 1, the plurality of sensor point openings comprising a generally oval shape as viewed in an axial direction.

11. A method of manufacturing a base plate of a medical appliance with selective sensor points, the method comprising:
forming a first adhesive layer comprising:
a stomal opening with a center point;
a proximal surface configured to be attached to a skin surface of a user; and
a plurality of sensor point openings arranged circumferentially around the center point at respective radial distances; and
arranging a plurality of electrodes distally of the first adhesive layer, the plurality of electrodes comprising:
a first leakage electrode and a second leakage electrode;
a sensing part of the first leakage electrode aligning with a first sensor point opening of the plurality of sensor point openings; and
a sensing part of the second leakage electrode aligning with a second sensor point opening of the plurality of sensor point openings to form a leak sensor;
wherein each of the plurality of sensor point openings extends through the first adhesive layer from the proximal surface to a distal surface of the first adhesive layer, thereby exposing sensing parts of the plurality of electrodes.

12. The method of claim 11, further comprising positioning a second adhesive layer distally of the first adhesive layer, the plurality of electrodes being located between the first adhesive layer and the second adhesive layer.

13. The method of claim 11, further comprising arranging a masking element between the second adhesive layer and the first adhesive layer, the masking element being more insulative than the first adhesive layer.

14. The method of claim 13, further comprising:
forming the masking element, the masking element comprising a second plurality of sensor point openings; and
wherein arranging the masking element between the second adhesive layer and the first adhesive layer comprises aligning each opening of the second plurality of sensor point openings with an opening of the plurality of sensor point openings of the first adhesive layer.

15. The method of claim 14, the second plurality of sensor point openings extending through the masking element.

16. The method of claim 11, the respective radial distances being generally equal distances from the center point.

17. A base plate for a medical appliance, comprising:
a first adhesive layer comprising:
a stomal opening with a center point;
a proximal surface configured to be attached to a skin surface of a user; and
a plurality of sensor point openings arranged circumferentially around the center point; and
a plurality of electrodes on a distal side of the first adhesive layer, the plurality of electrodes comprising:
a first leakage electrode comprising a first sensing part of a plurality of sensing parts; and
a second leakage electrode comprising a second sensing part of the plurality of sensing part that cooperates with the first sensing part to form a leak sensor;
wherein each of the plurality of sensor point openings extends entirely through the first adhesive layer, thereby exposing a corresponding sensing part of the plurality of sensing parts.

18. The base plate of claim 17, further comprising a masking element arranged between a second adhesive layer and the first adhesive layer, wherein the masking element is more insulative than the first adhesive layer.

19. The base plate of claim 18, wherein the masking element comprises a plurality of sensor point openings that each align with a corresponding sensor point opening of the first adhesive layer.

20. The base plate of claim 17, wherein the sensor point openings are arranged circumferentially around the center point at respective radial distances.

\* \* \* \* \*